United States Patent [19]

Hoeg et al.

[11] Patent Number: 5,441,732
[45] Date of Patent: * Aug. 15, 1995

[54] REVERSIBLE GELATION EMULSION COMPOSITIONS AND METHODS OF USE

[75] Inventors: Anne L. Hoeg, Havnegaten, Norway; David L. Meadows, Mission Viejo, Calif.

[73] Assignee: Allergan, Inc., Irvine, Calif.

[ * ] Notice: The portion of the term of this patent subsequent to Oct. 12, 2010 has been disclaimed.

[21] Appl. No.: 853,135

[22] Filed: Mar. 18, 1992

Related U.S. Application Data

[63] Continuation-in-part of Ser. No. 539,061, Jun. 15, 1990, Pat. No. 5,252,318.

[51] Int. Cl.[6] .................. A61K 31/19; A61K 31/745; A61K 47/38; A01N 25/04
[52] U.S. Cl. .................. 424/78.04; 514/912; 514/913; 514/914; 514/915; 514/938; 514/942
[58] Field of Search ............... 424/78.04, 422, 427, 424/428; 514/912, 913, 914, 915, 938, 942

[56] References Cited

U.S. PATENT DOCUMENTS

| | | | |
|---|---|---|---|
| 4,073,943 | 2/1978 | Wretlind et al. | 514/938 |
| 4,188,373 | 2/1980 | Krezanoski | 424/78 |
| 4,271,143 | 6/1981 | Schoenwald et al. | 424/78 |
| 4,407,792 | 10/1984 | Schoenwald et al. | 424/81 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,615,697 | 10/1986 | Robinson | 424/428 |
| 4,692,454 | 9/1987 | Mich et al. | 514/312 |
| 4,911,920 | 3/1990 | Jani et al. | 424/78 |
| 4,966,773 | 10/1990 | Gressel et al. | 424/489 |
| 5,252,318 | 10/1993 | Joshi et al. | 424/78.04 |

FOREIGN PATENT DOCUMENTS

| | | |
|---|---|---|
| 0028110 | 10/1980 | European Pat. Off. . |
| 0025202 | 3/1981 | European Pat. Off. . |
| 0068552 | 6/1982 | European Pat. Off. . |
| 0075540 | of 1983 | European Pat. Off. . |
| 0126684 | 11/1984 | . |
| 0227494 | of 1987 | European Pat. Off. . |
| 0300888 | of 1988 | European Pat. Off. . |
| 3440352 | of 1984 | Germany . |
| 59-122422 | 7/1984 | Japan . |
| 62-067017 | 3/1987 | Japan . |
| 02019310 | 1/1990 | Japan . |
| 223166 | 4/1990 | United Kingdom . |
| 89/0045 | of 1989 | WIPO . |
| 9000048 | 1/1991 | WIPO . |

OTHER PUBLICATIONS

European Patent Office, *Supplementary European Search Report EP 91 91 2727*, The Hague, 23 Feb. 1993, 6 pages.

*Primary Examiner*—Thurman K. Page
*Assistant Examiner*—Carlos Azpuru
*Attorney, Agent, or Firm*—Poms, Smith, Lande & Rose

[57] ABSTRACT

Reversibly gelling aqueous and oil emulsions are disclosed which can be modified to incorporate oil soluble pharmaceutical compounds for delivery to physiological systems in a soluble form and which undergo significant changes in viscosity in response to substantially simultaneous changes in both temperature and pH. The compositions are formed of relatively low concentrations of a stable combination of at least one pH-sensitive reversibly gelling polymer, at least one temperature-sensitive reversibly gelling polymer and at least one organic oil. The compositions can be formulated to exhibit a sol-gel transition over a wide range of conditions and viscosities and may be modified to incorporate a pharmaceutical compound for utilization as droppable or injectable drug delivery systems which will gel following administration to a physiological system for the sustained delivery of such pharmaceutical compounds.

22 Claims, 7 Drawing Sheets

EFFECT OF FLURBIPROFEN AND OIL CONTENT ON VISCOSITY OF EMULSION AT pH 4.0

EFFECT OF FLURBIPROFEN AND OIL CONTENT ON VISCOSITY OF EMULSIONS AT pH 7.4

REVERSIBLE GELATION EMULSION COMPOSITIONS AND METHODS OF USE

REFERENCE TO EARLIER APPLICATION

This application is a continuation-in-part of application Ser. No. 539,061, filed Jun. 15, 1990, now U.S. Pat. No. 5,252,318.

FIELD OF THE INVENTION

The present invention relates in general to macromolecular polymer mixtures exhibiting reversible gelation properties. More particularly, the present invention is directed to oil and water emulsion compositions that reversibly gel in response to simultaneous variations in at least two physical parameters such as temperature and pH or ionic strength. These compositions can be designed to reversibly gel at varying viscosities over a relatively wide range of conditions, making them particularly suitable for use as droppable, oral, or injectable drug delivery systems for the sustained and controlled delivery of oil soluble pharmaceutical medicaments and diagnostic agents.

BACKGROUND OF THE INVENTION

Various approaches to the production of reversibly gelling compositions have been developed over the years. Principal efforts have been devoted to the development of gelatinous drug delivery systems for topical and subcutaneous applications and, more recently, for the administration of ophthalmic drugs to the eye. In general, sustained release drug delivery systems incorporate pharmaceutical agents in solid or semi-solid vehicles which are applied to or implanted under the skin of a patient by medical personnel. However, unlike conventional drug delivery systems, ocular drug delivery systems also must address the additional problem of drug loss through the lacrimal drainage system as well as the needs of patient comfort and ease of administration. Additionally, pharmaceutical drugs have their maximum bioavailability when the drugs are delivered in soluble form. Thus, solid or semi-solid drug delivery systems carrying pharmaceutical drugs having little or no water solubility have the disadvantage of a low bioavailability of the drugs they deliver.

Early approaches to the solution of these problems, as exemplified by ocular drug delivery systems, utilized semi-solid ointments or gels applied directly to the conjunctiva or cul-de-sac of the eye to retain the pharmaceutical agents contained therein on the ocular surface against such physiological factors as tear turnover, tear drainage, blinking, and other mechanical losses. For example, U.S. Pat. Nos. 3,944,427 and 3,700,451 disclose gelatinous drug delivery compositions containing agar, xanthine gum, and carob gum in liquid mediums in order to enhance their residence time upon the skin or mucosae and the resultant bioavailability of the medicinal products contained therein. Similarly, European Patent Application No. 0 300 888 A1, filed Jul. 18, 1988, recently disclosed the use of rhamsan gum to thicken ophthalmic compositions for droppable and topical application.

While the majority of such prior art drug delivery vehicles were aqueous based, this created a problem for the delivery of water insoluble pharmaceutical compounds. Accordingly when formulated to deliver water insoluble drugs these prior art ointments and gels generally included low molecular weight alcohols or similar compounds which dissolved the water insoluble drug into a miscible form to produce an homogeneous system.

Though effective at increasing drug retention times, lack of patient acceptability remains a significant drawback to the use of such known drug delivery compositions in the eye. Many patients experience difficulty in applying the appropriate amount of such compounds to the eye and resist the unpleasant side effects of eyelid crusting and vision blurring. As a result, these compositions may only be suitable for use in the evening or during non-active hours. Additionally, semi-solid and gelatinous drug delivery systems which incorporate non-aqueous solvents such as low molecular weight alcohols for delivering water insoluble drugs are generally irritating to ocular and other sensitive tissues. This irritation generally is manifested in the form of stinging upon administration of the drug delivery system and excessive tearing when administered to the eye.

A known alternative drug delivery approach directed at solving the problems of eyelid crusting and vision blurring caused by applying viscous gel delivery vehicles is the use of a formulation which is liquid at room temperature but which forms a semi-solid when warmed to body temperature. Such a thermally triggered system is disclosed in U.S. Pat. No. 4,474,751, where an aqueous drug delivery system that forms a semi-solid "gel" at body temperature is formed from proprietary polymers known as "Tetronic ®" polyols. Generally speaking, these compositions are formed from approximately 10% to 50% of the specific polymers in an aqueous base. By adjusting the pH of these drug delivery systems through the addition of buffering agents, the gelling transition temperature can be raised to physiological temperatures on the order of 35° C. Similar drug delivery systems which can be injected subcutaneously or intramuscularly are disclosed in U.S. Pat. No. 4,474,752. These compounds also contain from 10% to 50% by weight Tetronic ® polymers and gel at temperatures from about 30° to 10° C.

A similar thermal setting gel drug delivery system also is described in U.S. Pat. No. 4,188,373, utilizing "Pluronic ® polyols" as the thermally gelling polymer. Adjusting the concentration of the polymer gives the desired "sol-gel" transition temperature to the composition. However, producing a compound which sets at physiologically useful temperature ranges limits the available viscosity of this gelled product.

Alternatively, it also has been proposed to utilize formulations which gel in response to changes in pH as drug delivery vehicles. By carefully controlling the pH of such mixtures, a solution which forms a gel upon mixing with aqueous tear fluid could theoretically be produced. However, it is believed that the relatively high buffering capacity of such pH responsive compositions can lead to slow gelling, irritation and discomfort when used in patient eyes.

Though generally successful at achieving increased drug retention times, it is known that the relatively high polymer concentrations required by known prior art formulations undesirably increases both the buffering capacity and the amount of thermal energy necessary to induce gelation of the compounds. This may lead to irritation and discomfort when these formulations are used on sensitive tissues such as in the eye. What is more, the high prior art polymer concentrations also contribute to unacceptably high product costs and generally slow the gelling process as well. This latter drawback may lead to migration of the compounds from the site of application or injection.

Additionally, because these known gelling systems are water based and utilize water soluble polymers, their use precludes delivering water insoluble drugs in a soluble form. Thus, the bioavailability of water insoluble drugs delivered from these gelling systems is substantially decreased and their effectiveness is correspondingly decreased.

Accordingly, it is a principal object of the present invention to provide reversibly gelling polymer compositions having significantly lower polymer concentrations than those previously attainable by the prior art. These lower concentrations reduce both the buffering and thermal capacities of the solutions to ensure their rapid and complete transition from liquid to gel upon application to physiological systems such as through an oral dosage, drop instillation to the surface of the eye, or through injection to an injectable drug depot.

It is a further object of the present invention to provide reversibly gelling compositions which can be utilized as drug delivery vehicles or wetting solutions that can be administered easily by a patient in the form of a freely flowing liquid or drops which gel immediately upon administration with minimal side effects. This provides the added benefits of ready patient control of drug dosage and improved patient acceptability.

It is a further object of the present invention to provide oral dosage, drop-instillable or injectable drug delivery vehicles suitable for delivering oil soluble drugs.

It is a further object of the present invention to provide reversibly gelling polymer compositions which can be utilized to deliver oil soluble drugs while maintaining a high degree of drug bioavailability and which prolong drug contact time for sustained drug release.

SUMMARY OF THE INVENTION

Generally stated, the present invention accomplishes the above-described objectives by providing aqueous compositions that reversibly gel in response to substantially simultaneous variations in at least two physical parameters such as temperature and pH or ionic strength. The compositions of the present invention can be tailored to exhibit a specific sol-gel transition over predetermined temperature and pH ranges to make the compositions particularly well suited for use as drop-instillable drug delivery systems, as well as for use as injectable sustained release drug delivery systems. What is more, the compositions of the present invention can be tailored to deliver water insoluble and water soluble pharmaceutical medicaments or diagnostic compounds in a soluble form with a resulting increase in bioavailability at the target site.

More particularly, it has been surprisingly discovered that superior reversibly gelling compositions can be produced from unusually low concentrations of uniquely synergistic polymer systems which stably exist in aqueous solutions. In contrast to prior art gelation systems that rely on only a single triggering mechanism which may be either changes in pH or changes in temperature, the compositions of the present invention reversibly gel in response to substantially simultaneous changes in both temperature and pH over predetermined ranges. What is more, the synergistic gelation action of the compositions of the present invention produces rapid and complete viscosity changes of at least an order of magnitude without the undesirable side effects associated with the high polymer concentration, single gelation mechanism compositions of the prior art.

It also has been discovered, that certain uniquely synergistic polymer systems which stably exist in aqueous solution can form oil and water emulsions without effecting their superior gelling properties. Moreover, these oil and water emulsions can incorporate water insoluble and oil soluble drugs into the emulsion and form homogeneous gels which deliver the drugs in a soluble, bioavailable form.

These properties make the compositions of the present invention particularly well suited for uses as topically applied lubricants and wetting agents as well as for drug delivery vehicles where sustained and controlled delivery of both water soluble and oil soluble bioactive agents is desired. For example, wetting agents, ocular drug delivery vehicles, and oral and injectable drug delivery compositions can be produced in accordance with the teachings of the present invention which exhibit steady state flow characteristics at or near room temperature and at pH ranges of 2.5 to 6.5, yet which almost instantaneously transform to highly visco-elastic gels when exposed to physiological conditions of pH and temperature on the order of pH 7.4 and 37° C.

Exemplary compositions are formed in accordance with the teachings of the present invention from aqueous compositions containing effective concentrations of a stable physical admixture or combination of at least one thermally-sensitive gelling polymer, and at least one pH-sensitive gelling polymer. The preferred compositions of the present invention additionally contain at least one organic oil in combination with at least one thermally-sensitive gelling polymer or one pH-sensitive gelling polymer which, preferably, is capable of acting as a surfactant for emulsifying the oil and water.

Thermally-sensitive gelling polymers for practicing the present invention can be selected from the group including alkyl cellulose, hydroxyalkyl cellulose, cellulosic ethers, Pluronic ® polymers and Tetronic ® polymers, with methylcellulose being particularly preferred. Exemplary pH-triggered gelling polymers that produce thickening at increased pH are preferably acidic polymers such as those containing carboxyl groups or lightly crosslinked carboxyl groups. Those skilled in the art will appreciate that small amounts of crosslinking agents such as divinyl benzene, divinyl glycol and polyalkenyl polyethers will facilitate the formation of 3D polymer network structures in the resultant crosslinked polyacrylates. Carboxy vinyl polymers such as polyacrylate, crosslinked polyacrylate acid, methacrylic acid, ethacrylic acid, $\beta$-methylacrylic acid, cis-$\alpha$-methylcrotonic acid, trans-$\alpha$-methylcrotonic acid, $\alpha$-butylcrotonic acid, $\alpha$-phenylacrylic acid, $\alpha$-benzylacrylic acid, $\alpha$-cyclohexylacrylic acid, and the like are examples of such acidic pH-sensitive gelling polymers. Conversely, where thickening is desired at decreased pH, polymers containing weakly basic pendant groups such as polyamine or poly-N-N-dimethylaminoethylmethacrylate may be employed.

Exemplary organic oils suitable for practicing the present invention include mineral oils, silicone oils, fatty acid oils, triglycerides, phthalate esters and fluorocarbon oils. Triglycerides and phthalates esters are particularly suitable due to their drug solubilizing forming capability. However, other biocompatible oils which form stable emulsions are contemplated as being within the scope of the present invention.

In contrast to the relatively high polymer concentrations required by the individually triggered prior art compositions (on the order of 10% or more by weight), the reversibly gelling compositions of the present invention preferably contain only approximately 0.25% to 5% by weight thermally-sensitive gelling polymer and only 0.1% to 0.5% by weight pH-sensitive gelling polymer. This substantially lower polymer concentration significantly reduces the amount of thermal energy required to induce gelation as well as reducing the buffering capacity of the compositions of the present invention. As a result, they are markedly superior topical wetting agents and drug delivery compounds.

However, it also is contemplated as being within the scope of the present invention to utilize thermally-sensitive gelling polymer concentrations ranging from approximately 0.1% to 30% by weight and pH-sensitive gelling polymer concentrations ranging from approximately 0.01% to 10% by weight. As discussed in detail below, these relatively broader polymer concentration ranges increase the scope of the available viscosities and sol-gel transition temperatures that may be produced in accordance with the teachings of the present invention. Thus, viscosities ranging from 200 to approximately 1 million cP at sol-gel transition temperatures ranging from 0° C. to 60° C. can be obtained with the present invention. For ophthalmic uses however, the previously described polymer concentration ranges are preferred.

The concentration of oil in the reversibly gelling emulsion compositions of the present invention can vary from 1% to 20% by weight. The combination of oil and reversibly gelling polymers utilized in the compositions of the present invention provide emulsions which are effective in delivering oil soluble pharmaceutical medicaments, diagnostic compounds or other agents in soluble forms. When utilized in the ocular milieu, the compositions of the present invention eliminate the discomfort, vision blurring and crusting produced by the known prior art compositions yet produce rapid conformational changes to high viscosity slow migrating compounds.

It also is contemplated as being within the scope of the present invention to utilize oil concentrations ranging from 5% to 15% by weight. This range of oil concentration range increases the concentrations and varieties of oil soluble pharmaceutical medicaments or diagnostic compounds available for delivery to a target site through the compositions of the present invention.

Accordingly, for use as drug delivery vehicles, the aqueous compositions of the present invention can be modified through the incorporation of suitable pharmaceutical medicaments or diagnostic compounds in concentrations ranging from approximately 0.0001% to 50% by weight. As those skilled in the art will appreciate, when compatible medicaments and/or diagnostic compounds are incorporated into the aqueous compositions of the present invention, the drugs will also be incorporated into the gelling matrix following delivery to the target site. As a result, the drug containing viscoelastic gel will reside at the applied location, thereby prolonging the retention and delivery of the incorporated drug.

Similarly, the aqueous and oil emulsion compositions of the present invention can be modified to incorporate oil soluble pharmaceutical medicaments in a soluble yet homogeneous form. Advantageously, the oil soluble drugs incorporated in the emulsion compositions remain homogeneously incorporated in the gelling matrix following delivery and gelation. Thus, the oil soluble pharmaceutical or diagnostic compounds are delivered in a form which enhances their bioavailability at the target site. Additionally, fine suspensions of solid drug compositions or particulate drug containing delivery systems may also be incorporated into the reversibly gelling compositions of the present invention. Injection into subcutaneous drug delivery depots or topical delivery by drop instillation of the solutions will then position such delivery systems at the site of choice for sustained delivery and bioavailability. This enhanced bioavailability and improved duration of action may lead to overall lower drug dosages being required with resultant improved side effect profiles.

Modifications to the viscosity ranges, pH ranges and temperatures at which the sol-gel transition takes place can be produced in the compositions of the present invention by varying the polymer concentrations as well as through the incorporation of small amounts of univalent or divalent salt. Typically, the addition of small quantities of salt giving a salt-to-combined polymer ratio up to 0.5 and preferably on the order of 0.045 to 0.075 will decrease the lower viscosity of the compositions if desired. Alternatively, it is contemplated as being within the scope of the present invention to incorporate up to approximately 0.2% to 0.9% by weight salt.

Further objects and advantages of the reversibly gelling emulsion compositions of the present invention, as well as a better understanding thereof, will be afforded to those skilled in the art from a consideration of the following detailed explanation of preferred exemplary embodiments thereof. Reference will be made to the appended sheets of drawings which will now be described briefly.

DETAILED DESCRIPTION OF PREFERRED EMBODIMENTS

Figure 1:
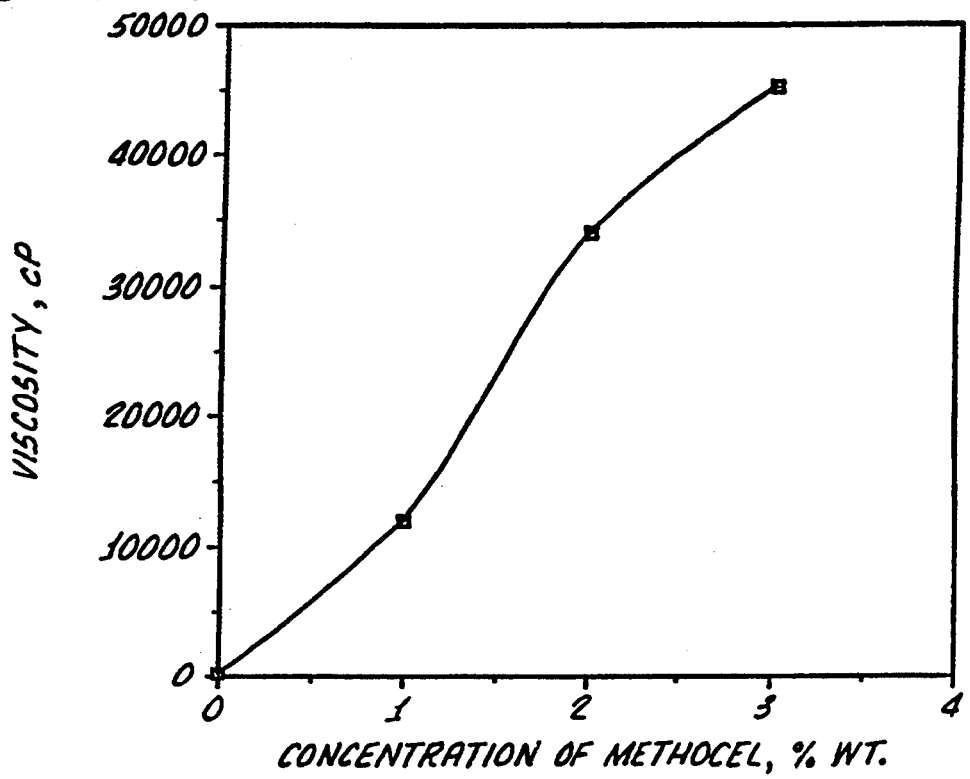
FIG. 1 is a graphical illustration showing the viscosity of a Methocel/Carbopol (Carbopol concentration fixed at 0.3% by weight) mixture as a function of the concentration of a Methocel at room temperature and pH 4.0 Carbopol.

The reversibly gelling aqueous compositions of the present invention are primarily intended for use as drop instillable, oral and injectable drug delivery vehicles as well as for topically applied lubricants, wetting agents and cleaning agents. Accordingly, the preferred exemplary embodiments of the present invention exhibit good, usable flow characteristics at room temperature, yet rapidly gel to highly visco-elastic compounds exhibiting viscosities several orders of magnitude greater at physiological temperatures and pH. The preferred exemplary embodiments of the present invention also exhibit enhanced solubility properties for oil soluble pharmaceutical medicaments and diagnostic compounds. Accordingly, the oil and water emulsions of the present invention can incorporate water insoluble, but oil soluble, pharmaceutical medicaments and diagnostic compounds for administration in a soluble form. This advantageously provides an increased bioavailability of the pharmaceutical medicament at the delivery site and a more efficacious delivery.

The preferred exemplary embodiments exhibit significant increases in viscosity in response to substantially simultaneous upshifts in both temperature and pH to those conditions encountered in the ocular milieu or at typical injectable drug delivery sites. However, those skilled in the art will appreciate that alternative compositions which gel in response to simultaneous increases in temperature and decreases in pH or the converse may also be produced in accordance with the teachings of the present invention where desired. Similarly, alternative compositions which gel at temperatures significantly above or below those encountered in physiological systems or which exhibit markedly different viscosities relative to those of the preferred embodiments may also be produced. Thus, for purposes of explanation and without limiting the scope of the present invention, the following exemplary embodiments will be discussed in the context of drop instillable or injectable reversibly gelling compounds intended for use in physiological systems.

As those skilled in the art will also appreciate, in addition to responding to changes in both temperature and pH, the ability to produce dramatic changes in viscosity with very small polymer concentrations is a significant feature of the present invention which overcomes many of the disadvantages associated with prior art compositions. For example, the polymer concentrations utilized in accordance with the teachings of the present invention significantly reduce the buffering capacity of the aqueous and oil emulsion compositions so produced, thereby effectively eliminating the irritation associated with high buffering capacity compounds such as the pH triggered gelling compositions of the prior art.

Similarly, reducing the polymer concentration also reduces the heat capacity of the reversibly gelling compositions and, as a result, the compositions of the present invention gel almost instantaneously upon application. This instantaneous gelation further reduces migration and loss of the compositions of the present invention over the prior art compounds. Moreover, the oil and water emulsion compositions of the present invention retain their emulsion characteristics upon gelling. The emulsion is not broken and the compositions remain homogeneous in a gelatinous state. As an additional benefit, the low polymer concentration compositions of the present invention produce transparent, colorless gels, making them particularly well suited for use as ocular drug delivery vehicles.

In its broadest capacity, an exemplary embodiment of the aqueous compositions of the present invention which exhibits reversible gelation in response to simultaneous variations in both temperature and pH over predetermined ranges comprises an aqueous solution incorporating a stable aqueous combination or admixture of at least one thermally-sensitive gelling polymer and at least one pH-sensitive gelling polymer in sufficient amounts to effectively produce reversible gelation over the desired temperature and pH ranges. Preferred thermally-sensitive gelling polymers include alkyl cellulose, hydroxyalkyl cellulose, cellulosic ethers, Pluronic® polymers and Tetronic® polymers, with methylcellulose being particularly preferred. Preferably, at least one of the thermally-sensitive gelling polymers or at least one of the pH-sensitive gelling polymer is capable of acting as a surfactant for emulsifying the organic oil discussed below.

Preferred pH-sensitive gelling polymers which increase viscosity with increasing pH are selected from the family of acidic and crosslinked acidic polymers such as those containing carboxyl groups, particularly carboxy vinyl polymers such as polyacrylates, crosslinked polyacrylate acid, methacrylic acid, ethacrylic acid, β-methylacrylic acid, cis-α-methylcrotonic acid, trans-α-methylcrotonic acid, α-butylcrotonic acid, α-phenylacrylic acid, α-benzylacrylic acid, α-cyclohexylacrylic acid, and the like.

Exemplary concentrations giving the widest range of viscosities and sol-gel transition temperatures range from approximately 0.1% to 40% by weight thermally-sensitive gelling polymer, and from approximately 0.01% to 10% by weight pH-sensitive gelling polymer. For physiological systems, the preferred exemplary concentrations giving the preferred sol-gel transition temperatures and associated viscosities range from approximately 0.1% to 5% by weight thermally-sensitive gelling polymer, and from approximately 0.01% to 0.5% by weight pH-sensitive gelling polymer.

In the preferred embodiments of the present invention, the aqueous combinations of thermally sensitive gelling polymer and pH-sensitive gelling polymer further include at least one organic oil to form stable oil and water emulsions. Suitable organic oils include pharmaceutically acceptable mineral oils, silicone oils, and vegetable oils such as peanut, olive, sesame, corn, and cottonseed oil. Also suitable are esters of medium chain fatty acids such as the Miglyol ® product line of triglycerides, glyceryl esters, phthalate esters, such as diethyl phthalate and dibutyl phthalate and propylene glycol diesters. The oils are preferably present at a concentration ranging from approximately 1% to approximately 20% by weight.

Thus, an exemplary composition of the present invention comprises an homogeneous association complex of a macromolecular mixture of methylcellulose, a polysaccharide available from Dow Chemical under the trade name Methocel, and a lightly cross-linked polyacrylic acid such as Carbopol 940, a hydrophilic acrylic polymer available from the B. F. Goodrich Company and Miglyol 812 ® a triglyceride of 8 to 10 carbon fatty acids available from Huls America located in Chicago, Ill. Methocel consists of cellulose chains with a moderate to high degree of hydrophobic methyl group substitution. This characteristic additionally provides Methocel with some surfactant characteristics which aid in the formation of the oil and water emulsion. Carbopol is a hydrophilic acrylic polymer which easily dissolves in water.

When these polymers and mineral oil are mixed in the preferred exemplary concentrations ranging from 0.1% to 10% by weight Carbopol, from 0.01% to 30% by weight Methocel, and from 1% to 20% by weight Miglyol 812 ® a stable combination of the aqueous polymer mixture and the Miglyol 812 ® oil component is formed. This is in direct contrast to the teachings of the prior art wherein aqueous polymer mixtures are extremely difficult, if not impossible, to form due to molecular interaction and precipitation. More importantly, by varying the concentration ranges of this aqueous composition, a wide variety of viscosities and sol-gel transition temperatures and pHs can be produced.

For example, at formation conditions, the pH of the composition will generally range from approximately 2.5 to 6.5, with a preferable range of 4.0 to 5.5. The osmolality will generally range from 20 to 500, with a preferable range between approximately 50 to 400. The osmolality can be adjusted through the addition of physiologically acceptable salts and non-ionic additives such as sodium chloride, potassium chloride, calcium chloride, magnesium chloride, sodium lactate, magnesium phosphate, mannitol, sucrose and glycerine. However, sodium chloride is the preferred tonicity adjuster.

More significantly, at temperatures ranging from 0° C. to 45° C., and preferably between 15° C. to 30° C., the viscosity of the compositions can be adjusted to range from 20 to 40,000 cP (measured at a shear rate of 2.6 sec$^{-1}$), with a preferred range of between 100 to 30,000 cP producing drop instillable or injectable viscous fluids. Taking these same formulations and exposing them to physiological conditions of a pH at approximately 7.4 and a temperature of approximately 37° C. results in rapid gelation producing viscosities ranging from 200 to 1 million cP with preferable ranges between approximately 50,000 to 400,000 cP. As a result, the compositions of the present invention can be tailored to produce drop instillable ocular wetting agents, cleaning agents or drug delivery systems which will remain in the eye or at the target site for from fractions of an hour to ten hours or more, and, preferably for from two to six hours.

More specifically, when mixed in the exemplary aqueous concentrations of approximately 1% to 3% by weight methylcellulose and 0.2% to 0.4% by weight Carbopol, a stable combination of the aqueous polymer is formed which exhibits a viscosity on the order of 10,000 cP at room temperature (25° C.) and at a pH of between 3.0 and 5.0. When this composition is subjected to physiological temperatures and pH on the order of 37° C. and pH 7.4 two simultaneous intermolecular conformational changes are believed to occur. First, increased ionization produces unwinding of the coils of the acrylic chain. This is accompanied by the expulsion of the hydrophobic functional components of the methylcellulose chain. As a result, within approximately 60 to 120 seconds a three-dimensional network is formed with a concomitant increase in visco-elasticity of several orders of magnitude to approximately 140,000 cP. As those skilled in the art will appreciate, oil droplets, compatible medicaments, diagnostic compounds and microfine particulate drug delivery vehicles incorporated into the liquid composition will be entrapped in the visco-elastic polymer matrix so produced for sustained release applications where desired.

Furthermore, exemplary oil and water emulsions of the present invention exhibit similar viscosity characteristics. Thus, a composition of approximately 1 wt % methyl cellulose, 0.3wt % carbopol, and from 5wt % to 15wt % Miglyol 812 ® has a viscosity on the order of 10,000 cP at a rate of 2.6 sec$^{-1}$ at room temperature and at a pH of 4. When this composition is subjected to 37° C. and a pH of 7.4, the viscosity increases to about 90,000 cP. Moreover, oil and water emulsion compositions of approximately 1 wt % methyl cellulose, 0.3wt % Carbopol, and from approximately 5 wt % to 15 wt % oil selected from peanut oil, dibutyl phthalate, and diethyl phthalate have similar viscosity characteristics at pH 4.0 and pH 7.4. The presence of the oil does not significantly change the viscosity characteristics and the concomitant increase in viscosity characteristics with increases in pH and temperature.

That such significant increases in viscosity should occur with such low polymer concentrations in response to simultaneous changes in both temperature and pH comes in complete contrast to the teachings of the prior art. As noted above, prior art systems for which high viscosity changes are induced by temperature change alone require preparations with high polymer concentrations typically much greater than 10% by weight. What is more, with such high concentrations, the heat capacity of the ocular milieu and the heat transfer limitations of the preparations themselves may result in relatively slow or incomplete viscosity increases. Moreover, the high polymer concentrations of the prior art may cause discomfort, polymer crusting on the eyelids, vision blurring, and altered anatomical conditions such as blockage of the lacrimal duct. Similarly, systems for which viscosity changes are induced by pH changes alone typically require high polymer concentrations as well. These pH-triggered systems exhibit a significantly greater buffering capacity than the thermally-triggered systems. In the ocular milieu this high buffering capacity may lead to incomplete gelation and local irritation.

Accordingly, the compositions of the present invention are significantly advantageous over known systems in three major ways. First, for use in physiological conditions, the compositions of the present invention can have significantly less total polymer content; second, these compositions effectively utilize both the buffering and heat capacity of the ocular milieu to rapidly and completely induce conformational changes leading to substantially higher viscosity; and, third, these compositions can deliver oil soluble pharmaceutical medicaments and diagnostic agents in a soluble form, thereby increasing their bioavailability.

As with the compositions of the present invention in general, the rheological properties of the exemplary aqueous compositions of thermally-sensitive methylcellulose and pH-sensitive polyacrylate are affected by the molecular weights of the respective polymers, their concentration, temperature, pH and the presence of other solutes. However, it should be emphasized that the properties of the aqueous compositions of the present invention are uniquely and unexpectedly synergistic.

More specifically, because methylcellulose is non-ionic, in solution alone it is visco-elastically stable over a wide range of pH from approximately 3 to 11. The viscosity of polyacrylate solutions alone is proportional to the polymer concentration, both at lower and higher pH. For example, at polymer concentrations between 0.1% and 0.4% by weight, aqueous polyacrylate solutions are very inviscid over a pH range of 3 to 7. Additionally, aqueous solutions containing more than 0.5% by weight polyacrylate have a much higher buffer capacity and need additional neutralizing base to increase their viscosity. However, mixtures of such pH-sensitive and thermally-sensitive polymers in accordance with the teachings of the present invention exhibit viscosities which are substantially in excess of the sum of the individual viscosities of the individual aqueous polymer solutions at both lower and higher pH. Thus, at pH 4.0, the viscosity of a 3% by weight methylcellulose solution measured with a Carri-Med rheometer at a shear rate of approximately 2.6 sec$^{-1}$ is approximately 18,000 cP. Similarly, the viscosity of a 0.2% Carbopol solution at pH 4.0 is approximately 50 cP. The viscosity of the mixture of these two polymers produced in accordance with the teachings of the present invention at pH 4.0 is approximately 30,000 cP. As those skilled in the art will appreciate, 30,000 cP is substantially greater than the anticipated combined viscosity of 18,050 cP.

The rheological properties of the exemplary water and oil emulsion compositions of thermally-sensitive methylcellulose, pH-sensitive polyacrylate, and oil exhibit the same uniquely and unexpectedly synergistic properties as those compositions which do not include mineral oils. Moreover, the presence of oil and the formation of an emulsion does not significantly alter the rheological properties of the polymeric solutions of the present invention. Additionally, small variations in the amount of oil do not affect the gelling properties of the aqueous and oil emulsions. For example, at pH 3.8 the viscosity of an aqueous solution of 0.5% by weight Carbopol 940 and 0.5% by weight Methocel A15 is approximately 22,250 cps at 25° C. The viscosity of an aqueous and oil emulsion of 0.5% by weight Carbopol 940, 0.5% by weight Methocel A15 and 5% by weight mineral oil at pH 3.5 and 25° C. is approximately 26,250 cps. When the pH and temperature of these compositions are raised the former composition gels to a viscosity of approximately 91,270 cps at a pH of 7.4 and a temperature of 37° C. and the latter composition gels to a viscosity of approximately 97,000 cps at a pH of 7.6 and a temperature of 37° C.

The rheological properties that can be expected with exemplary aqueous compositions of the present invention utilizing a formulation of Methocel A4M methylcellulose and Carbopol 940 are listed in Table I. Similarly, Table II is an illustrative listing of the rheological properties that can be expected with oil and water emulsions utilizing an exemplary formulation of Methocel A4M, Carbopol 940 and mineral oil.

TABLE 1

Viscosity for Typical Methocel (1% by Weight)/Carbopol (0.3% by Weight) Preparation

| | Temperature | | | |
|---|---|---|---|---|
| | 25° C. | | 37° C. | |
| pH | 4.0 | 7.4 | 4.0 | 7.4 |
| Viscosity, cP | 11,500 | 90,800 | 20,000 | 140,000 |

(shear rate approximately 2.6 sec$^{-1}$)

TABLE II

Viscosity Data for Carbopol ®/Methocel ® Gels Containing 5% Mineral Oil

| Sample | | | | | |
|---|---|---|---|---|---|
| % 940 | % A4M | % Oil | pH | °C. | Viscosity cP |
| 0.3 | 1 | 0 | 4.01 | 25 | 9560 |
| 0.3 | 1 | 5 | 3.95 | 25 | 12890 |
| 0.3 | 1 | 0 | 7.43 | 25 | 108460 |
| 0.3 | 1 | 5 | 7.37 | 25 | 120170 |

Figure 2:
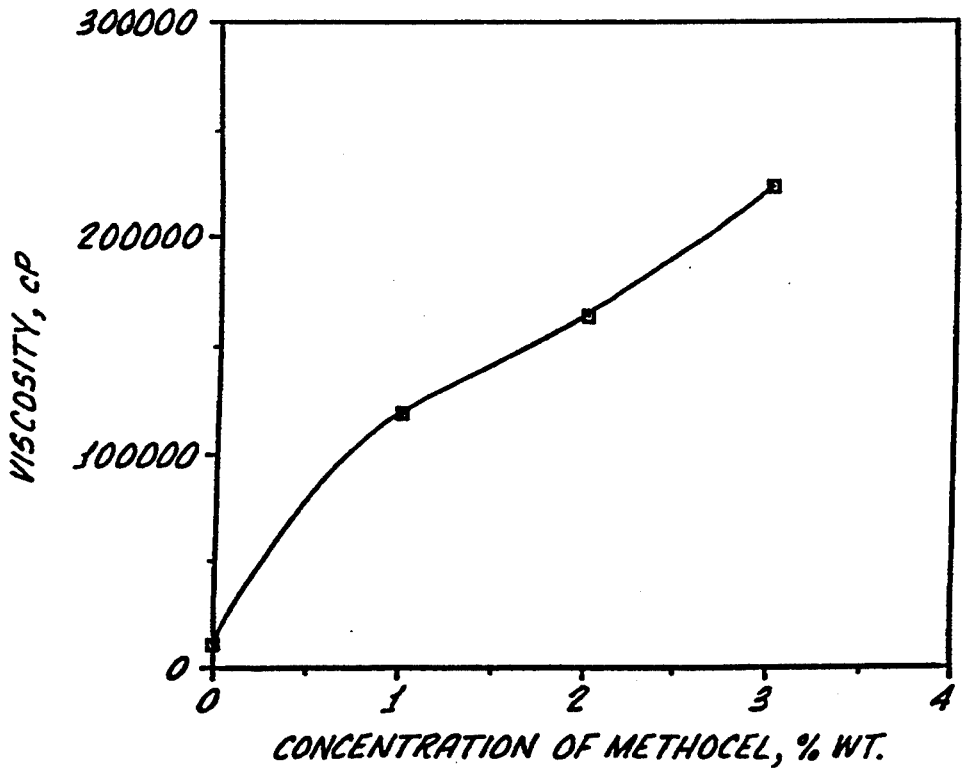
FIG. 2 is a graphical illustration showing the viscosity of a Methocel/Carbopol (Carbopol concentration fixed at 0.3% by weight) mixture as a function of the concentration of a Methocel at 37° C. and pH 7.4 Carbopol.

FIGS. 1 and 2 more clearly show the rheologic properties of exemplary Methocel/Carbopol mixtures. The viscosity of an aqueous Methocel/Carbopol composition is plotted as a function of the concentration of Methocel (the Carbopol concentration being fixed at 0.3% by weight) at room temperature and pH 4 in FIG. 1 and at 37° C. and pH 7.4 in FIG. 2. As shown in FIG. 1, aqueous compositions exhibiting a viscosity ranging from approximately 20 to in excess of 40,000 cP can be produced at room temperature and pH 4 which, as shown in FIG. 2, gel to viscosities ranging from approximately 200 to well in excess of 200,000 at physiological conditions. As those skilled in the art will also appreciate, the foregoing temperature and pH conditions discussed in Table 1 are exemplary of those present at room temperature (25° C.) and in the ocular milieu where the surface of the eye is bathed with isotonic lacrimal fluid at pH 7.4 and approximately 37° C. Thus, it is readily apparent that the composition disclosed in Table 1 is a freely-flowing viscous liquid at its formulation temperature and pH which, upon contact with tear fluid and physiologic conditions, forms a highly visco-elastic gel.

Additionally, the highly visco-elastic gels formed at the physiologic temperature and pH are transparent with a specific gravity of approximately 1.01 and a refractive index of approximately 1.33. Thus, the aqueous compositions of the present invention can easily be administered to the eye in drop form and will rapidly gel under the combined effect of both temperature and pH when placed in the eye thereby preventing their rapid elimination from the eye through the lacrimal drainage system. Moreover, the favorable optical properties and low polymer concentration of the compositions should cause minimal or no visual perturbation once gelled in situ. It should also be appreciated that these gelled compositions exhibit a mucoadhesive property which further aids their retention in the cul-de-sac of the eye. Also, the gelled polymers are self-lubricating and relatively soft and deformable which increases patient comfort and acceptability.

Figure 3:
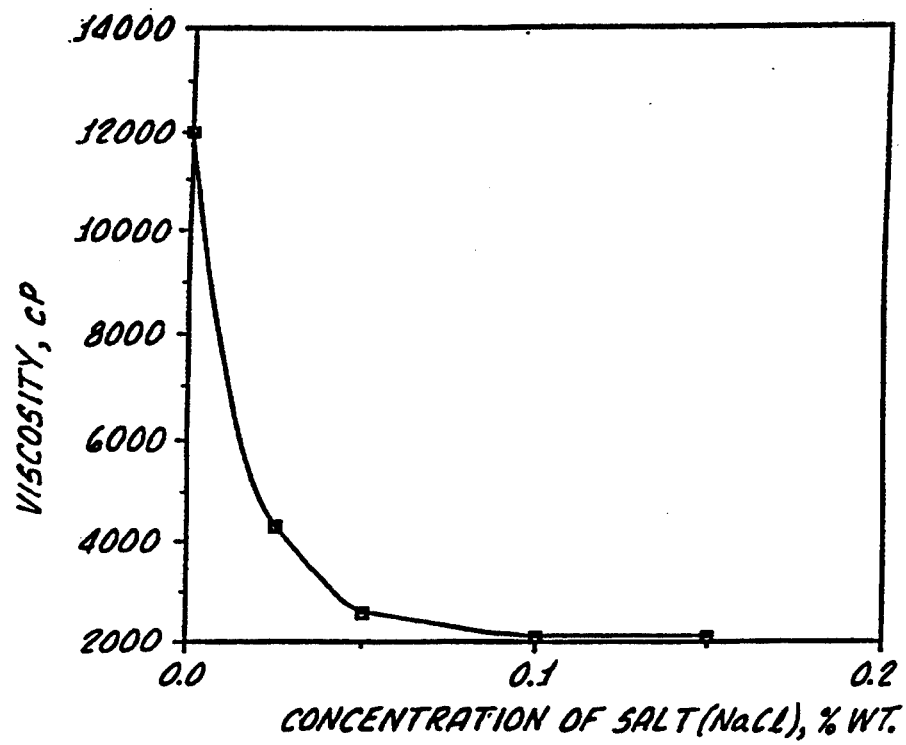
FIG. 3 is a graphical illustration showing the viscosity of a Methocel (1%)/Carbopol (0.3%) mixture as a function of salt concentration at room temperature and pH 4.0.
Figure 4:
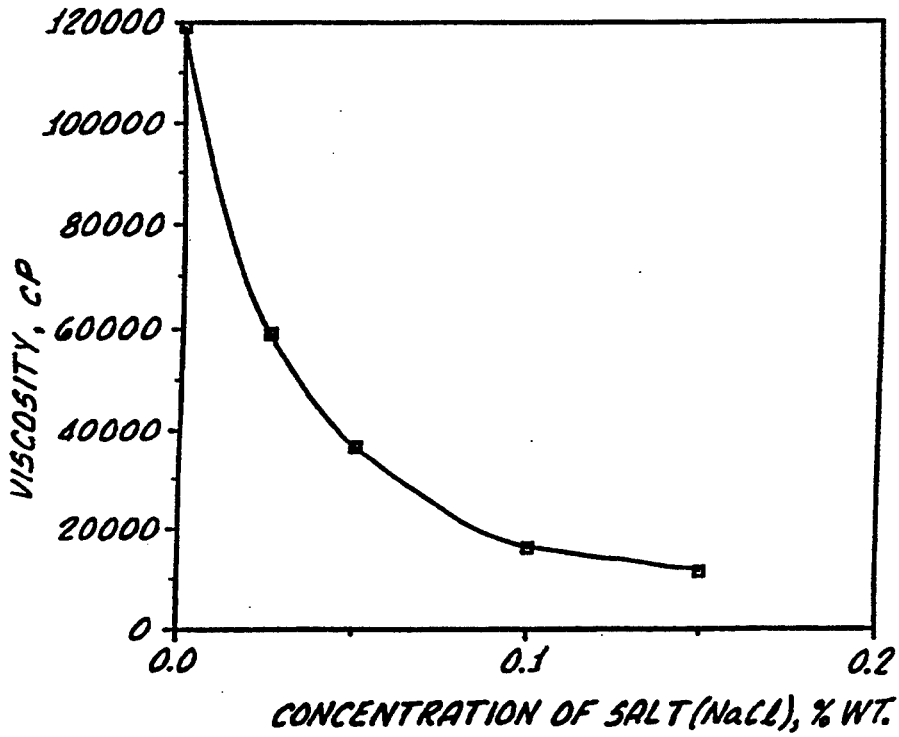
FIG. 4 is a graphical illustration showing the viscosity of a Methocel (1%)/Carbopol (0.3%) mixture as a function of salt concentration at 37° C. and pH 7.4.

It should also be noted that the viscosity of the aqueous compositions can be modified by adding a pharmaceutically acceptable salt such as mono- or di-valent salts including sodium chloride, potassium chloride, calcium chloride or mixtures thereof, as well as suitable alkali metal salts such as sodium sulfate and the like. Preferred salt to total polymer ratios will range from 0 to approximately 0.5 and preferably from approximately 0.045 to 0.075. As shown in FIGS. 3 and 4, the addition of salt exhibits its most significant relative effect on the lower viscosity of the aqueous system. For example, slight increases in the salt concentration apparently preferentially decrease the lower viscosity ranges while exhibiting a comparatively minor decrease on the upper viscosity ranges.

Figure 5:
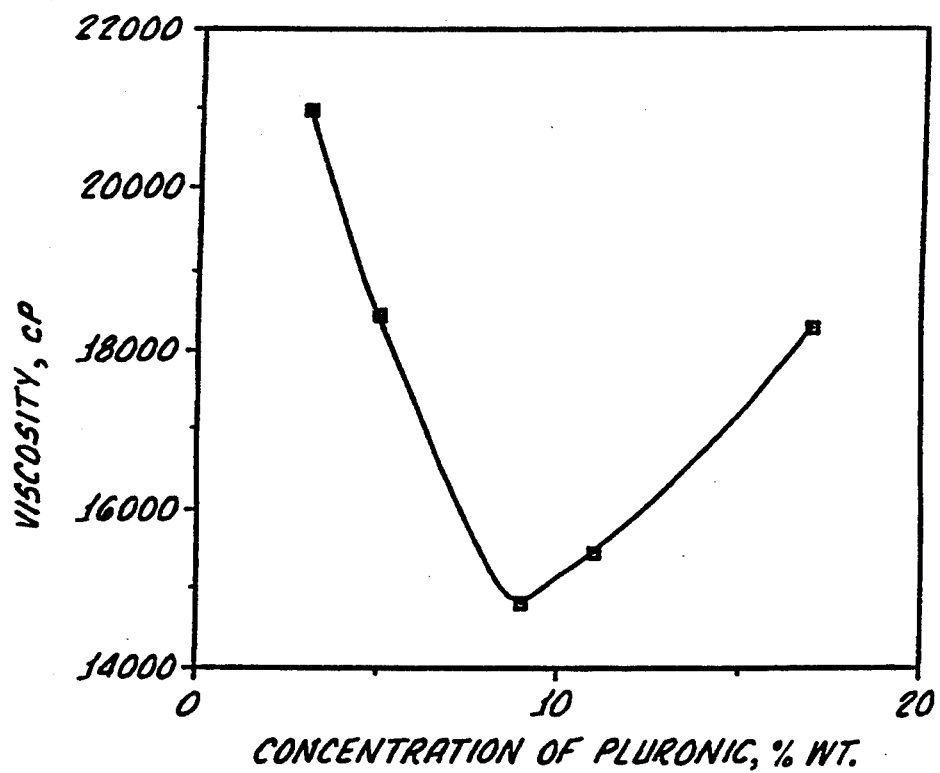
FIG. 5 is a graphical illustration showing the viscosity of a Pluronic ®/Carbopol (Carbopol concentration fixed at 0.3% by weight) mixture as a function of the concentration of Pluronic ® at room temperature and pH 5.0 Carbopol.
Figure 6:
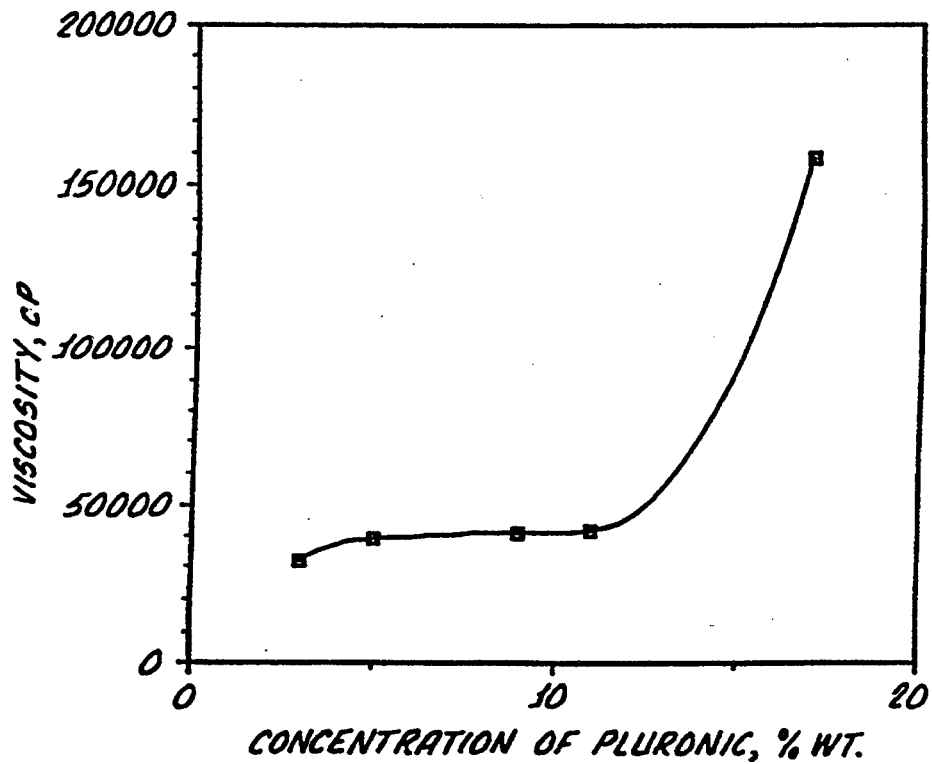
FIG. 6 is a graphical illustration showing the viscosity of a Pluronic ®/Carbopol (Carbopol concentration fixed at 0.3% by weight) mixture as a function of the concentration of Pluronic ® at 37° C. and pH 7.4 Carbopol.

The rheological properties of alternative exemplary compositions produced in accordance with the teachings of the present invention are illustrated in FIGS. 5 through 8. FIGS. 5 and 6 illustrate the viscosity of a Pluronic ®/Carbopol opol mixture prepared in accordance with the teachings of the present invention. Pluronic ® polymers are block copolymers of propylene oxide and ethylene oxide and are thermally-sensitive gelling polymers. It is contemplated as being within the scope of the present invention to form reversibly gelling aqueous compositions comprising stable mixtures of from 0.01% to 10% by weight pH-sensitive gelling polymers such as Carbopol, and from approximately 1% to 30% by weight Pluronic ® polymer. As shown in FIGS. 5 and 6, such mixtures form viscous liquids at room temperature and pH 5 and rapidly gel to highly visco-elastic gels at physiologic conditions.

Figure 7:
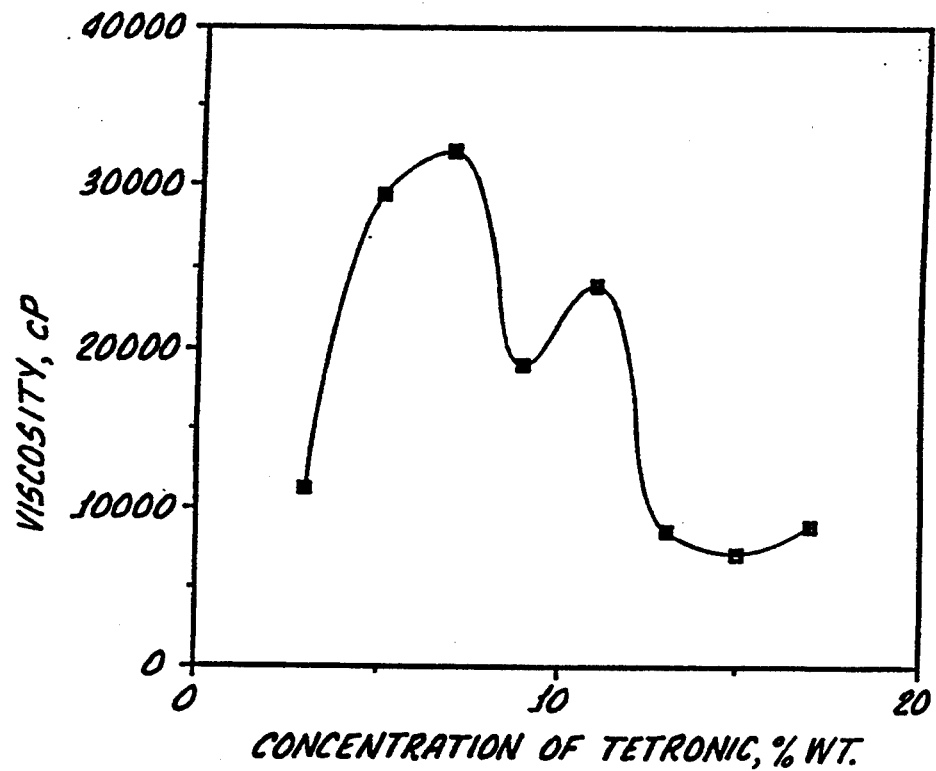
FIG. 7 is a graphical illustration showing the viscosity of a Tetronic ®/Carbopol (Carbopol concentration fixed at 0.3% by weight) mixture as a function of the Tetronic® concentration at room temperature and pH 5.0 Carbopol.
Figure 8:
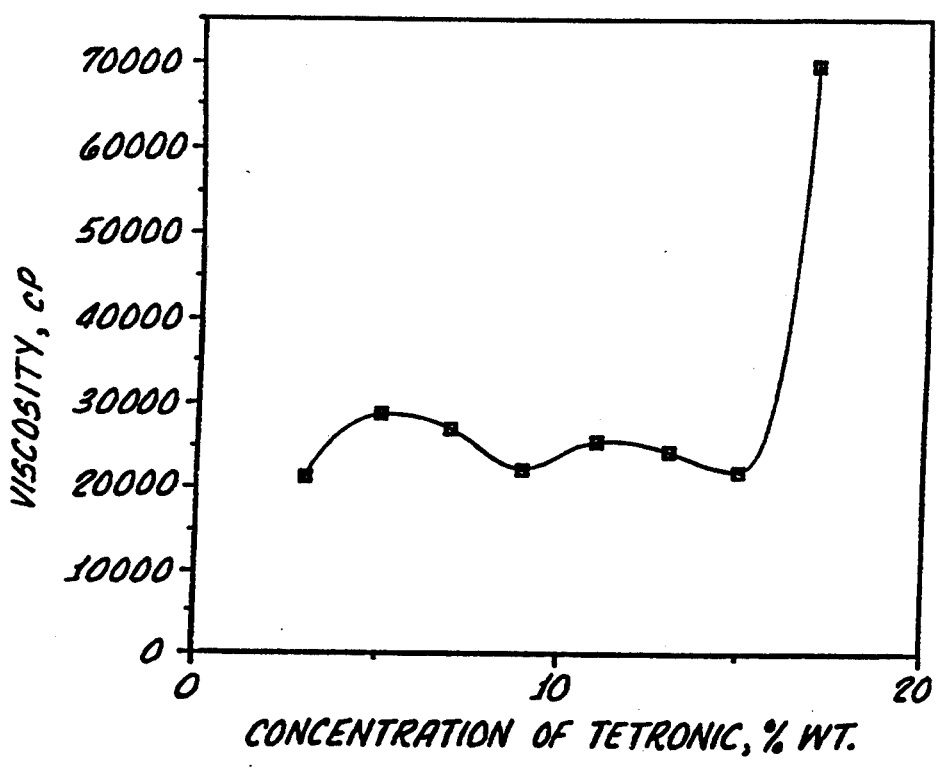
FIG. 8 is a graphical illustration showing the viscosity of a Tetronic®/Carbopol (Carbopol concentration fixed at 0.3% by weight) mixture as a function of the Tetronic® concentration at 37° C. and pH 7.4 Carbopol.

Similarly, alternative compositions can be formulated within the scope of the present invention utilizing Tetronic ® polymers. Tetronic ® polymers are tetrafunctional block copolymers derived from the sequential addition of propylene oxide and ethylene oxide to ethylenediamine. As shown in FIGS. 7 and 8, reversibly gelling aqueous compositions produced in accordance with the teachings of the present invention utilizing Tetronic ® polymers can also be formulated to remain liquid at room temperature and lower pHs on the order of 4.0 to 5.5 while gelling to highly visco-elastic gels at physiological conditions. It should be noted that these alternative polymer compositions extend the temperature ranges available for gelling and formulation without significantly modifying the pH and osmolality conditions associated with these compositions.

Though the foregoing exemplary compositions all reversibly gel in response to simultaneous upshifts in both temperature and pH, it is also possible to utilize the teachings of the present invention to produce aqueous compositions which are liquid at higher pH and lower temperatures and gel at lower pH (neutral or lower) and higher temperatures. For example, polymers containing weakly basic pendant groups such as amine containing polymers of poly-N,N dimethylaminoethyl methacrylate can be combined with methylcellulose, Pluronic ® or Tetronic ® polymers or combinations thereof as well as with organic oils to form emulsions. Such combinations will be liquid at higher pH and lower temperature while gelling at lower pH and higher temperature.

The aqueous compositions of the present invention may be utilized as wetting agents or lubricants for contact lenses or the treatment of conditions such as dry eye. However, it is preferred that the compositions be utilized as drug delivery vehicles for administering a variety of pharmaceutical medicaments and diagnostic compounds. Moreover, it should again be emphasized that the compositions of the present invention are particularly well suited for delivering hydrophobic or water insoluble pharmaceutical compounds.

The most promising drugs for incorporating into the aqueous drug delivery compositions of the present invention are levobunolol, pilocarpine, dipivefrin and others which exhibit poor bioavailability. Water insoluble steroids such as prednisone acetate, Medrysone, flurbiprofen and fluorometholone are particularly suitable for incorporation into the aqueous and oil emulsions of the present invention as well. Other exemplary drugs or diagnostic agents which can be administered by the aqueous compositions of the present invention include, but are not limited to:

(1) antibacterial substances such as beta-lactam antibiotics, such as cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamicin, kanamycin, amikacin, sisomicin and tobramycin; nalidixic acid and analogs such as norfloxacin and the antimicrobial combination of flucalanine/pentizidone; nitrofurazones, and the like;

(2) antihistaminic and decongestants such as pyrilamine, chlorpheniramine, tetrahydrazoline, antazonline, and the like;

(3) anti-inflammatorics such as cortisone, hydrocortisone, hydrocortisone acetate, betamethasone, dexamethasone, dexamethasone sodium phosphate, prednisone, methylpredinisolone, medrysone, fluorometholone, fluocortolone, prednisolone, prednisolone sodium phosphate, triamcinolone, indomethacin, sulindac, its salts and its corresponding sulfide, and the like;

(4) miotics and anticholinergics such as echothiophate, pilocarpine, physostigmine salicylate, diisopropylfluorophosphate, epinephrine, dipivolyl epinephrine, neostigmine, echothiophate iodide, demecarium bromide, carbachol, methacholine, bethanechol, and the like;

(5) mydriatics such as atropine, homatropine, scopolamine, hydroxyamphetamine, ephedrine, cocaine, tropicamide, phenylephrine, cyclopentolate, oxyphenonium, eucatropine, and the like; and other medicaments used in the treatment of eye conditions or diseases such as (6) antiglaucoma drugs, for example, betaxalol, pilocarpine, timolol, especially as the maleate salt and R-timolol and a combination of timolol or T-timolol with pilocarpine. Also included are epinephrine and epinephrine complex or prodrugs such as the bitartrate, borate, hydrochloride and dipivefrin derivatives and hyperosmotic agents such as glycerol, mannitol and urea;

(7) antiparasitic compounds and/or anti-protozoal compounds such as ivermectin; pyrimethamine, trisulfapyrimidine, clindamycin and corticosteroid preparations;

(8) antiviral effective compounds such as acyclovir, 5-iodo-2'-deoxyuridine (IDU), adenosine arabinoside (Ara-A), trifluorothymidine, and interferon and interferon inducing agents such as Poly I:C;

(9) carbonic anhydrase inhibitors such as acetazolamide, dichlorphenamide, 2-(p-hydroxyphenyl)thio-5-thiophenesulfonamide, 6-hydroxy-2-benzothiazolesulfonamide and 6-pivaloyloxy-2-benzothiazolesulfonamide;

(10) anti-fungal agents such as amphotericin B, nystatin, flucytosine, natamycin, and miconazole;

(11) anesthetic agents such as etidocaine cocaine, henoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

(12) ophthalmic diagnostic agents such as
  (a) those used to examine the retina and chloride-sodium fluorescein;
  (b) those used to examine the conjunctiva, cornea and lacrimal apparatus such as fluorescein and rose bengal; and
  (c) those used to examine abnormal pupillary responses such as methacholine, cocaine, adrenaline, atropine, hydroxyamphetamine and pilocarpine;

(13) ophthalmic agents used as adjuncts in surgery such as alpha-chymotrypsin and hyaluronidase;

(14) chelating agents such as ethylenediamine tetraacetate (EDTA) and deferoxamine;

(15) immunosuppressive agents and anti-metabolites such as methotrexate, cyclophosphamide, 6-mercaptopurine, and azathioprine;

(16) peptides and proteins such as atrial natriuretic factor, calcitonin-gene related factor, luteinizing hormone, releasing hormone, neuroterisin, vasoactive intestinal peptide, vasopressin, cyclosporine, interferon, substance P enkephalins, epidermal growth =factor, eye-derived growth factor, fibronectin, insulin-like growth factor and mesodermal growth factor;

(17) lubricating agents such as sodium hyaluronate; and

(18) combinations of the above such as antibiotic/anti-inflammatory as in neomycin sulfate-dexamethasone sodium phosphate, concomitant anti-glaucoma therapy such as timolol maleate-aceclidine.

Because the drug delivery compositions of the present invention are uniquely suited for utilization in a wide variety of physiological applications such as the ocular, oral, nasal, rectal or subcutaneous administration of pharmaceutical compounds, a wide variety of pharmaceutical agents may be incorporated therein. Accordingly, the foregoing listing of pharmaceutical agents is not intended to limit the scope of the present invention and is exemplary only.

Preferably, when utilized as an aqueous drug delivery vehicle for drop instillation, oral administration or injection, the compositions of the present invention can be modified to include from approximately 0.0001% to 50% by weight pharmaceutical medicament or diagnostic agent. To prepare an aqueous drug delivery vehicle in accordance with the teachings of the present invention, an appropriately effective amount of the pharmaceutical compound of choice is simply incorporated into the aqueous composition at the composition formulation temperatures and pHs. Preferably, the compound of choice will be soluble in the solution or will be homogeneously dispersed and will not react with the polymer system. Soluble pharmaceutical compounds will readily dissolve in the aqueous composition, whereas insoluble compounds will be particularized for even dispersion throughout the compositions. Preferably oil soluble compounds are incorporated into aqueous and oil emulsions and form a stable homogeneous composition.

Along these lines, it is also contemplated as being within the scope of the present invention to incorporate insoluble or erodible microparticulate drug delivery systems such as those known in the art into the aqueous compositions. In this manner, controlled release drug delivery systems can be incorporated into the aqueous compositions of the present invention and retained in position when administered by drop or injection.

Following gelation, the medicament or diagnostic agent or the oil droplets containing same will be incorporated into the gelled polymer matrix and will remain on site for sustained drug delivery as the solidified gel slowly erodes and the incorporated pharmaceutical agent diffuses out into the surrounding lacrimal or physiological fluid. Additionally, it should be noted that by varying the concentration of pharmaceutical compound within the aqueous composition, it is possible to modify and control the quantity of pharmaceutical compound delivered by drop or injection. For example, a liquid drug delivery vehicle can be prepared in accordance with the teachings of the present invention containing from about 0.01 to about 5% of the medicament or pharmaceutical agent of choice on a weight to weight basis. For drop instillation methodologies the drop size will preferably range from approximately 20 $\mu$l to 50 $\mu$l, with 25 $\mu$l drops being particularly preferred. Thus, from one drop of the liquid composition which contains about 25 $\mu$l of solution, one would obtain about 0.0025 mg to about 1.25 mg of drug.

The following non-limiting examples are offered as being illustrative of the properties of exemplary compositions of the present invention. In the following examples, concentrations are expressed in weight percent (% w/w), deionized water is utilized to make the formulations, and the formulation temperatures are 25° C.

EXAMPLE I

Thirty gm of water was heated to about 90° C. To this heated water, 3 gm of Methocel A4M (available from Dow Chemicals, Midland, MI) was added and the mixture was stirred until the polymer particles were thoroughly wetted and evenly dispersed. Sixty-seven gm cold water was added to lower the temperature of the dispersion to about 10° C. for complete solubilization. The final mixture was brought to 100 gm of total weight by adding deionized water to give 3% w/w of Methocel mixture. The resultant mixture was stirred for two hours at 2.5 rpm.

In a separate container, 0.9 gm of Carboxypolymethylene (available from B. F. Goodrich, Cleveland, Ohio, as Carbopol 940) was completely dispersed and stirred in 90 gm of deionized water. The mixture was agitated at 100 rpm for two hours following which water was added to bring the final mixture weight to 100 gm and 0.9% w/w of Carbopol content.

A physical admixture of 20 gm of the 3% w/w of Methocel solution (prepared as mentioned above) and 20 gm of the 0.9% w/w Carbopol solution was prepared. 0.06 gm of Levobunolol was dissolved in 18 gm of deionized water and added to the physical admixture of the polymers. The resultant drug containing aqueous solution was then titrated with 5N NaOH to pH 4.5 following which the final formulation was brought to 60 gm by adding deionized water. The resultant formulation was as follows: 1% Methocel, 0.3% Carbopol and 0.1% Levobunolol. The viscosity was measured using a Carri-Med Rheometer and a rheogram depicting shear stress v/s shear rate was obtained. The formulation had a viscosity of 12,000 cP at a shear rate of 2.64/sec. The mixture was a smooth flowing liquid having droppable characteristics.

EXAMPLE II

Methocel A4M mixture, 3% w/w, was prepared as set forth under Example I. Forty grams of this solution was blended with 0.12 gm of Carbopol 940, 0.6 gm of Levobunolol and 18 gm of deionized water. The mixture was then stirred at 50 rpm at room temperature for 15 hours. The resultant drug containing mixture was titrated with 5N NaOH to pH 4.2 following which deionized water was added to bring the final formulation weight to 100% (60 gm) followed by stirring at 50 rpm for another two hours. The final formulation obtained was as follows: 2% Methocel, 0.2% Carbopol and 0.1% Levobunolol. The viscosity was measured using a Carri-Med Rheometer and a rheogram depicting shear stress v/s shear rate was obtained. The formulation had a viscosity of 7806 cP at a shear rate of 2.64/sec. The mixture was a smooth flowing liquid having droppable characteristics.

EXAMPLE III

Methocel A4M mixture, 3% w/w, was prepared as set forth under Example I. A preblend of 0.06 gm of salt (Sodium Chloride) and 0.06 gm of Levobunolol was prepared. Forty gm of Methocel solution was blended with 0.18 gm of Carbopol 940, the preblend of salt and Levobunolol and 16 gm of water. The mixture was then stirred at 50 rpm for 15 hours and then titrated with 5N NaOH to pH 4.00. The final formulation was brought to 100% weight (60 gm) by adding deionized water and stirred at 50 rpm for another two hours. The final formulation obtained was as follows: 2% Methocel, 0.3% Carbopol, 0.1% Sodium Chloride and 0.1% Levobunolol. The viscosity was measured using a Carri-Med Rheometer and a rheogram depicting shear stress v/s shear rate was obtained. The formulation had a viscosity of 8317 cP at a shear rate of 2.65/sec. The mixture was a smooth flowing liquid having droppable characteristics.

EXAMPLE IV

Methocel A4M mixture, 3% w/w, was prepared as set forth under Example I. A preblend of 0.06 gm of Levobunolol and 0.18 gm of Carbopol 940 was prepared. A physical admixture of 20 gm of the 3% w/w of Methocel solution and the preblend was prepared, followed by adding 38 gm of deionized water. The mixture was stirred for 15 hours at 50 rpm to assure complete mixing. The resultant drug containing aqueous solution was then titrated with 5N NaOH to pH 4.12 following which the final formulation was brought to 60 gm by adding deionized water followed by mixing for two hours at 50 rpm. The resultant formulation was as follows: 1% Methocel, 0.3% Carbopol and 0.1% Levobunolol. The viscosity of the formulation was measured using a Carri-Med Rheometer and a rheogram depicting shear stress v/s shear rate was obtained. The formulation had a viscosity of 3154 cP at a shear rate of 2.55/sec. The mixture was a smooth flowing liquid having droppable characteristics.

EXAMPLE V

Thirty gm of water was heated to 90° C. To this heated water, 5 gm of Methocel A4M was added and the mixture was stirred until the polymer particles were thoroughly wetted and evenly dispersed. The remainder of the water, 67 gm, was added as cold water to lower the temperature of dispersion to about 10° C. for complete solubilization. The final mixture was brought to 100 gm of total weight by adding purified water to give 5% w/w of Methocel mixture. The resultant mixture was stirred for two hours at 25 rpm.

Twenty grams of deionized water was measured and to this 0.12 gm of Carbopol EX-55 (available from B. F. Goodrich) was added. The solution was stirred at 50 rpm for two hours until all the Carbopol was dispersed into the solution. Thirty-six grams of 5% Methocel solution, as prepared above, was added to the Carbopol solution followed by the addition of 0.09 gm of Sodium Chloride. The physical admixture was stirred for 12 hours at 50 rpm to ensure complete mixing and dispersion of the polymers. The mixture was then titrated with 5N NaOH to pH 3.53 following which the final formulation was brought to 100% weight. The final formulation by weight percent was: 3% Methocel, 0.2% Carbopol, 0.15% Sodium Chloride. The viscosity of the formulation was measured using a Carri-Med Rheometer and a rheogram depicting shear stress v/s shear rate was obtained. The formulation had a viscosity of 16,610 cP at a shear rate of 2.64/sec. The mixture was a smooth flowing liquid having droppable characteristics.

EXAMPLE VI

Methocel A4M mixture, 5% w/w, was prepared as set forth under Example V. A preblend of 0.12 gm of Carbopol EX-55 and 0.14 gm of Sodium Chloride was prepared. This preblend was added to 36 gm of the 5% w/w of Methocel solution followed by the addition of 20 gm of water. The mixture was stirred at 50 rpm for 15 hours and then titrated with 5N NaOH to pH 3.5. The final formulation was then brought to 100% weight by adding deionized water and further stirred for two hours at 50 rpm. The final formulation by weight percent was: 3% Methocel, 0.2% Carbopol, 0.25% Sodium Chloride. The viscosity was measured using a Carri-Med Rheometer and a rheogram depicting shear stress v/s shear rate was obtained. The formulation had a viscosity of 16,600 cP at a shear rate of 2.85/sec. The mixture was a smooth flowing liquid having droppable characteristics.

EXAMPLE VII

Methocel A4M mixture, 3% w/w, was prepared as set forth under Example I. Carbopol EX-55 (available from B. F. Goodrich), 0.12 gm, was dispersed in 18 gm of deionized water. After complete dispersion, 0.09 gm of Sodium Chloride was added to this Carbopol solution and the resultant mixture was stirred at 50 rpm for 10 hours. Forty grams of 3% Methocel was then added to the Carbopol-Salt solution and the mixture stirred for four hours. The resultant mixture was then titrated with 5N NaOH to pH 4.49 following which deionized water was added to bring the final formulation to 100% weight (60 gm). The final formulation by weight percent was: 2% Methocel, 0.2% Carbopol, 0.15% Sodium Chloride. The viscosity was measured using a Carri-Med Rheometer and a rheogram depicting shear stress v/s shear rate was obtained. The formulation had a viscosity of about 11,500 cP at a shear rate of 2.64/sec. The mixture was a smooth flowing liquid having droppable characteristics.

EXAMPLE VIII

An exemplary aqueous gel mixture was prepared containing 3% Methocel A4M, 0.3% Carbopol (940) and 0.2% salt with a 1% loading of Acid Orange 8 dye for an in vitro release kinetic study. A 0.4 gram solidified gel sample of this composition was placed in a USP dissolution kettle (paddle speed 50 rpm) containing 500 ml phosphate buffer at pH 7.4 and 37° C. The dissolution time for the gel was observed to be in excess of nine hours. A $T_{50}$ value of approximately 55 minutes and a $T_{90}$ value of approximately 200 minutes was obtained from the dye release profile of the gel.

EXAMPLE IX

An analysis of in vivo gel retention time was undertaken utilizing rabbit eyes. The gel mixture of Example 1 was tagged with high molecular weight FITC dextran (MW approximately 70,000). Gel formation after installation of a 50 microliter drop appeared to be quite rapid and led to the formation of a continuous coating on the pre-corneal surface of the eye by the gel matrix. Photographic and biomicroscopic assessments were obtained over a seven hour observation period. Two significant retention times of the delivery vehicle in the rabbit eye were obtained: (1) a distinct gelatinous formation in the lower cul-de-sac; and (2) a smooth, apparently uniform film over the ocular surface. The distinct gel formation lasted for approximately three hours while the uniform film retention time was 0 to 6.5 hours or more.

EXAMPLE X

Sodium fluorescein was used as a marker with the composition of Example 2 to monitor its penetration into the anterior chamber of the eye. The rabbit eye anterior chamber was monitored using a slit lamp technique and an incremental increase in fluorescence over a period of seven hours after the installation of the gel labelled with fluorescein was observed.

EXAMPLE XI

Probe acute toxicological studies did not reveal any toxicity issues. No irritation, injection, staining or cytotoxicity was observed with the gel mixture in rabbit eyes. Ocular status was noted to be healthy after 24 hours post-installation.

EXAMPLE XII

An exemplary drug delivery vehicle incorporating erodible microparticulate drug delivery vehicles was prepared as follows. Levobunolol was blended into a heated slurry of poly(orthoester) and cooled to solidify the mixture. The drug containing poly(orthoester) was found to produce microparticulates ranging in size from 1 to 300 μm. These particles were physically dispersed in the exemplary reversible gelling composition of Example I to produce a reversibly gelling drug delivery vehicle incorporating erodible drug containing microparticulates.

EXAMPLE XIII

An exemplary therapeutic agent for the treatment of severe keratoconjunctivitis sicca was produced from an aqueous composition containing 1% by weight Methocel, 0.3% by weight Carbopol 940, and 0.1% by weight sodium hyaluronate and isotonically adjusted with glycerol at pH 4.5 to 5.5. Upon installation of a 50 μl drop in rabbit eyes, almost instantaneous gelation was observed. Examination of the rabbit eyes 24 hours following installation indicated healthy ocular status.

EXAMPLE XIV

An experiment designed to test the operability of utilizing an aqueous and oil emulsion in a pH-sensitive and thermally-sensitive gelling system was performed in the following manner. An aqueous 1% by weight Methocel A15 solution was prepared by dissolving the appropriate amount of Methocel A15 in deionized water at approximately 90° C. and then cooled. Similarly, an aqueous 1% by weight Carbopol 940 solution was prepared by dissolving the appropriate amount of Carbopol 940 in deionized water. Equal volumes of the two separate solutions were combined to form a single mixture having polymer concentrations of 0.5% each. The mixture was initially a white milky non-viscous suspension. After the pH was raised to approximately 4 by adding 5N NaOH a clear colorless solution formed. The viscosity of this solution was measured at a shear rate of 2.6 1/sec and a temperature of 25° C. on a Carrimed viscometer. Samples were retained to measure the viscosity after the pH and temperature of the solution was raised to approximately 7.5 and 37° C. respectively.

EXAMPLE XV

An aqueous solutions of 0.5% by weight Methocel A15 and 0.5% by weight carbopol 940 was prepared in a manner similar to the procedure described in Example XIV except that 5% by weight mineral oil was also incorporated into the solution and mixed to form a stable emulsion. The viscosity of the oil and water emulsion was measured at a pH of approximately 4° at 25° C. and again at a pH of approximately 7.5 at a temperature of 37° C. Viscosity measurements determined that the synergistic gelling properties of the aqueous solution did not significantly change with the addition of mineral oil and the formation of an emulsion.

EXAMPLE XVI

A number of different oil and water emulsions containing a variety of oils and different amounts of each oil were evaluated for their stability at room temperature. The emulsions were prepared by adding a controlled amount of oil to an aqueous solution of 1% by weight Methocel A4M and 3% by weight Carbopol 950. The resulting oil and water composition was mixed for 5 minutes with a Brookfield counter-rotating mixer at a constant mixing speed. Each of the resulting mixtures was then visually evaluated for stability. Table III illustrates the results obtained for each of four different oils at five different concentrations.

TABLE III

| | Emulsion Stability at Room Temp. | | | | |
| | % Oil (w/w) | | | | |
| OIL | 5 | 10 | 15 | 20 | 40 |
|---|---|---|---|---|---|
| Miglyol 812 ® | stable | stable | stable | unstable | unstable |
| Peanut Oil | stable | stable | stable | unstable | not done |
| Dibutyl Phthalate | stable | stable | stable | unstable | not done |
| Diethyl Phthalate | stable | stable | stable | unstable | not done |

EXAMPLE XVII

Figure 9:
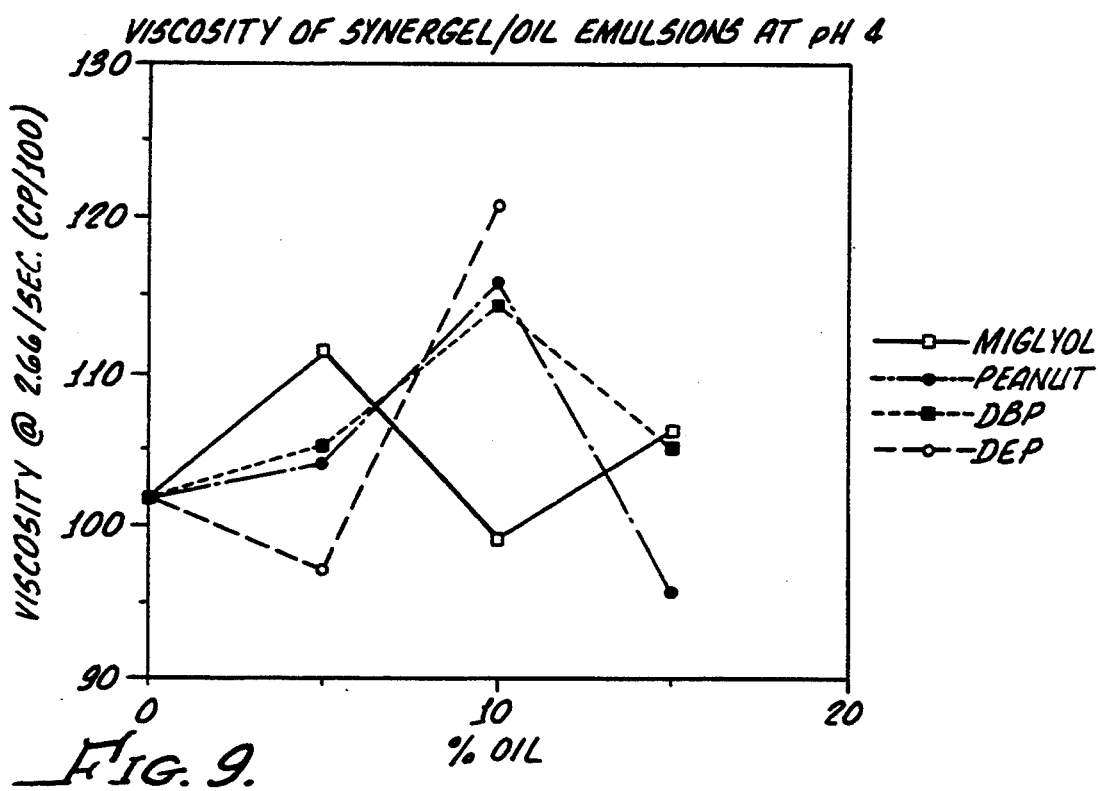
FIG. 9 is a graphical illustration showing the viscosity of stable oil and water emulsions at pH 4 for four different oils as a function of oil concentration.
Figure 10:
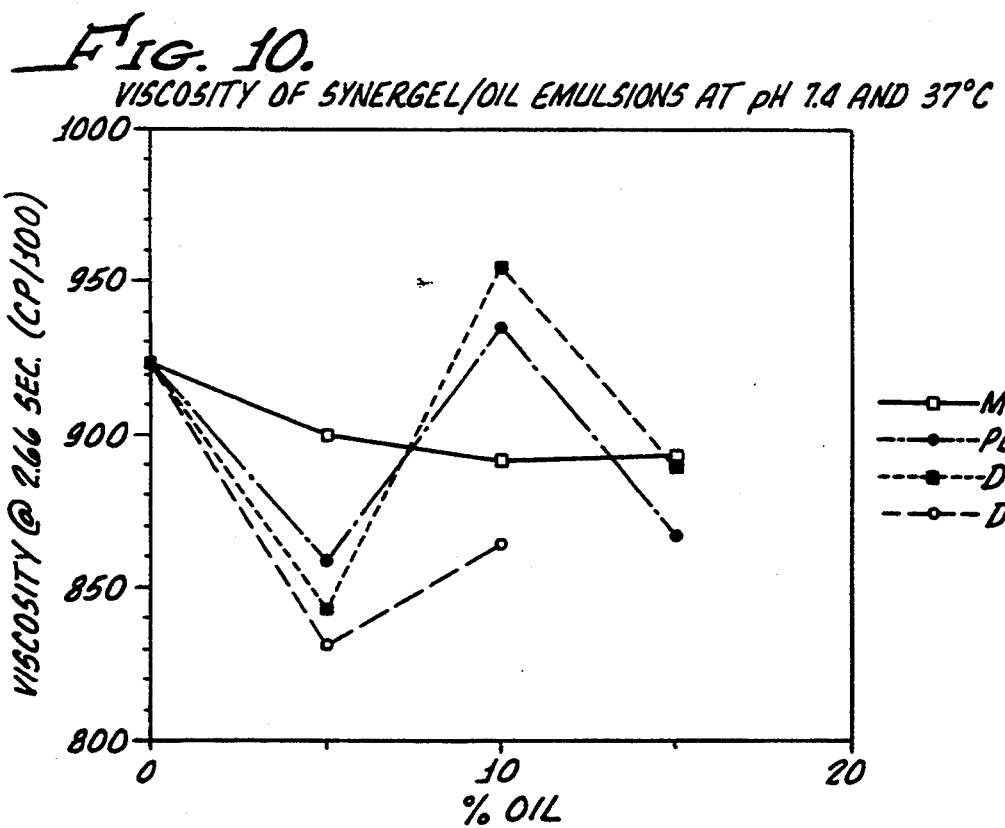
FIG. 10 is a graphical illustration showing the viscosity of stable oil and water emulsions at pH 7.4 for four different oils as a function of oil concentration.

Each of the stable emulsions prepared in Example XVI above was tested for viscosity and yield point on a Carri-Med Rheometer using a 4 cm, 4° SS cone at a shear rate of 2.66 sec$^{-1}$. Viscosity data were obtained at pH 4 and 25° C. Then the pH was adjusted to 7.4, the temperature raised to 37° C., and the viscosity measured again. FIG. 9 is a graph illustrating the viscosities for each stable emulsion at pH 4 and 25°. FIG. 10 similarly illustrates the viscosities for each stable emulsion at pH 7.4 and 37° C.

EXAMPLE XVIII

In order to further evaluate the long term stability of the emulsions of the present invention, repeat viscosity data were obtained after storing each of the stable emulsion prepared in Example XVI for 15 days at room temperature. Table IV illustrates the viscosity of each of the emulsions as a percentage of the initial value. Viscosity measurements for the emulsions containing 5% by weight and 10% by weight oil did not change by more than ±20% from their initial measurements.

TABLE IV

Stability of Emulsions at pH 4

| % Oil | Miglyol 812 | Peanut Oil | Dibutyl Phthalate | Diethyl Phthalate |
|---|---|---|---|---|
| 5 | 102% | 97% | 110% | 96% |
| 10 | 99% | 119% | 94% | 104% |

EXAMPLE XIX

In order to determine the feasibility of delivering both fluorometholone and flurbiprofen (in the free acid form) in a reversibly gelling oil and water emulsion the solubility of these two drugs in two different oils, Miglyol 812 and diethyl phthalate was determined. Table V illustrates the results of the solubility tests.

TABLE V

Drug Solubility in Oil at Room Temperature

| Drug | Miglyol | Diethyl Phthalate |
|---|---|---|
| Fluorometholone | <0.001% | 0.075% |
| Flurbiprofen (free acid) | 2–4% | 12–20% |

The solubility of fluorometholone in diethyl phthalate is relatively low, but because the drug has a high potency, this solubility level is acceptable.

EXAMPLE XX

Flurbiprofen, a non-steroidal antiinflammatory drug, was evaluated for its effect on the viscosity of emulsions containing Miglyol. The emulsions were prepared by adding the appropriate amount of Miglyol to an aqueous solution of 1% by weight Methocel A4M and 0.3% by weight Carbopol 950 and mixing. Viscosities and yield points were determined at pH 4 and pH 7.4 at a rate of 2.66 sec$^{-1}$ for emulsions containing 5% by weight Miglyol and 10% by weight Miglyol as well as between 0% by weight and 0.10% by weight flurbiprofen. Table VI illustrates the data obtained from the viscosity and yield point tests.

TABLE VI

Effect of Flurbiprofen on Miglyol Emulsions

| % Flurbiprofen | Viscosity (cP) pH 4 | Viscosity (cP) pH 7.4 | Yield Point (dyne/cm$^2$) pH 4 | Yield Point (dyne/cm$^2$) pH 7.4 |
|---|---|---|---|---|
| | 5% Miglyol | | | |
| 0.00 | 11,100 | 80,000 | 114 | 738 |
| 0.01 | 9,000 | 54,500 | 66 | 414 |
| 0.03 | 8,300 | 27,400 | 54 | 144 |
| 0.10 | 8,400 | 27,600 | 63 | 180 |
| | 10% Miglyol | | | |
| 0.00 | 11,100 | 80,000 | 114 | 738 |
| 0.01 | 8,800 | 67,800 | 48 | 558 |
| 0.03 | 8,800 | 44,500 | 54 | 288 |
| 0.10 | 8,900 | 29,000 | 75 | 198 |

Figure 11:
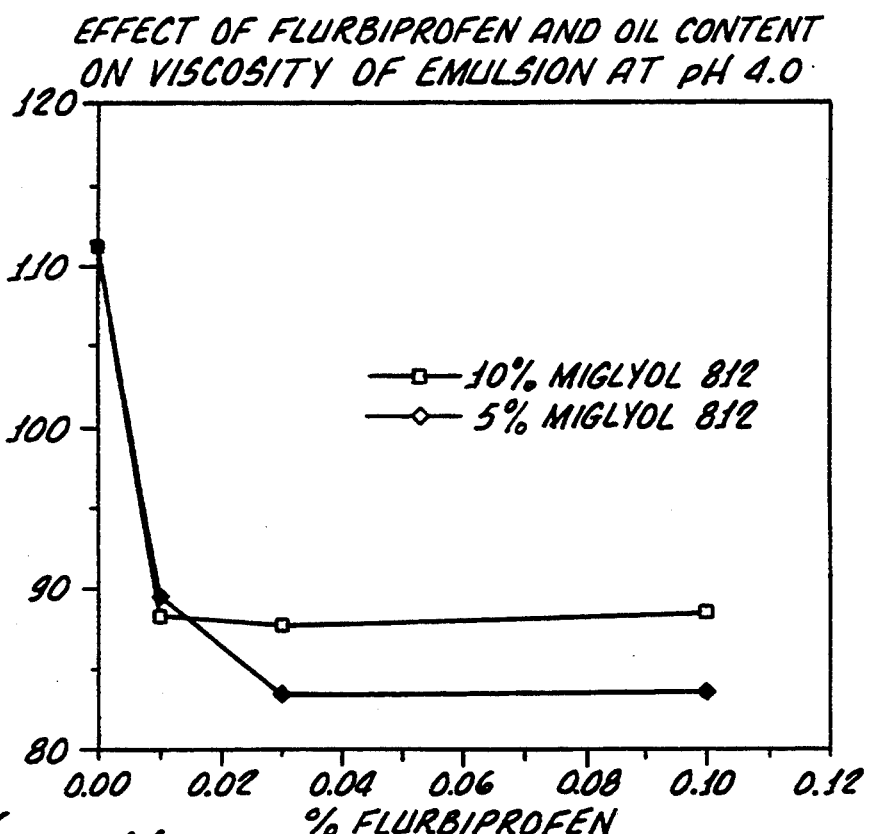
FIG. 11 is a graphical illustration showing the viscosity at pH 4.0 emulsions of Miglyol 812, Methocel, Carbopol, flurbiprofen and water as a function of flurbiprofen concentration and Miglyol 812 concentration.
Figure 12:
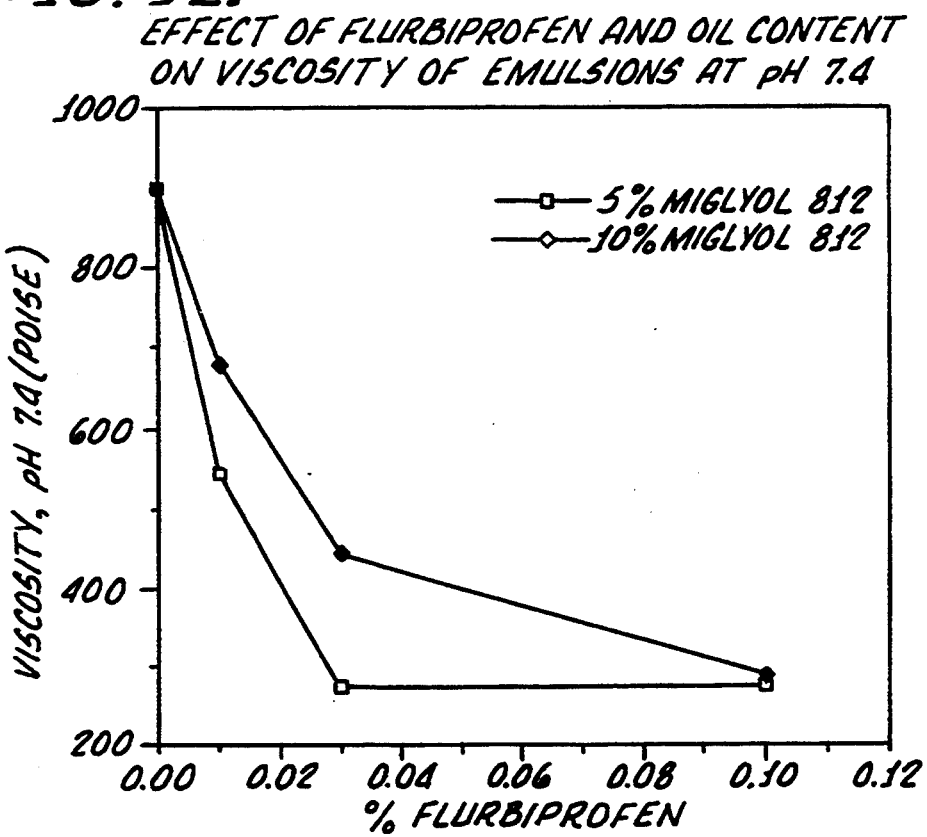
FIG. 12 is a graphical illustration showing the viscosity at pH 7.4 of emulsions of Miglyol 812, Methocel, Carbopol, flurbiprofen and water as a function of flurbiprofen concentration and Miglyol 812 concentration.

The data in Table VI indicate that the emulsion viscosity is pH dependent and flurbiprofen concentration dependent. This is expected since the emulsion viscosity is dependent on the concentration of ionic species and flurbiprofen is a weak acid having a very small water solubility at pH 4.0 and a higher water solubility at pH 7.4. At higher ph's the ionic species concentration increases, and with increasing flurbiprofen incorporated in the emulsion, there is a more profound decrease in viscosity. However, even with emulsion concentrations of flurbiprofen as high as 0.1% by weight, the effect of the reversibly gelling Carbopol in increasing the emulsion viscosity with increases in pH outweighs the viscosity decreasing effect of the drug. FIG. 11 and FIG. 12 graphically illustrate the decrease in viscosity associated with the increase in flurbiprofen concentration at pH 4.0 and pH 7.4

EXAMPLE XXI

Figure 13:
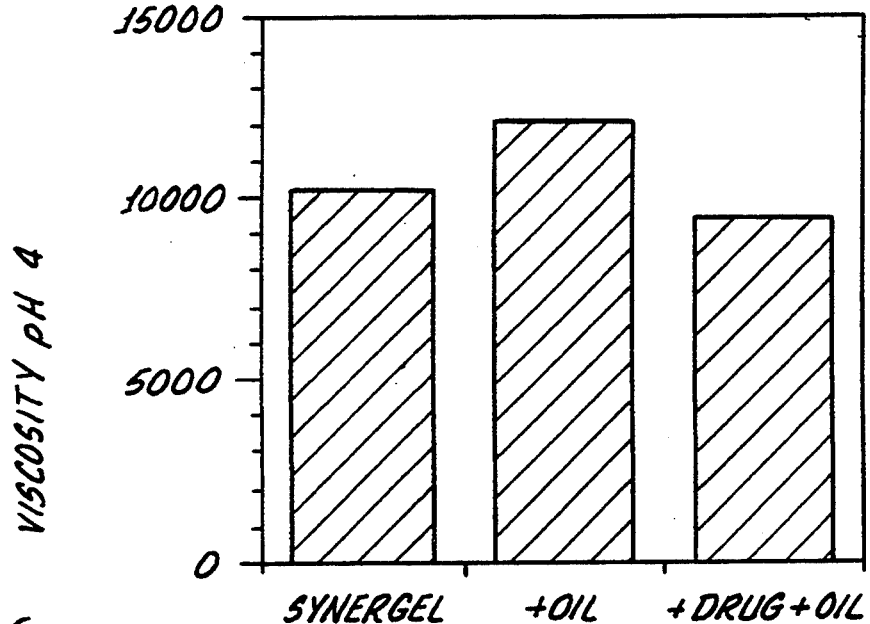
FIG. 13 is a bar graph illustrating the effect of 0.075 wt % fluorometholone on the viscosity of an emulsion of diethyl phthalate, water, Methocel and Carbopol at pH 4.0.
Figure 14:
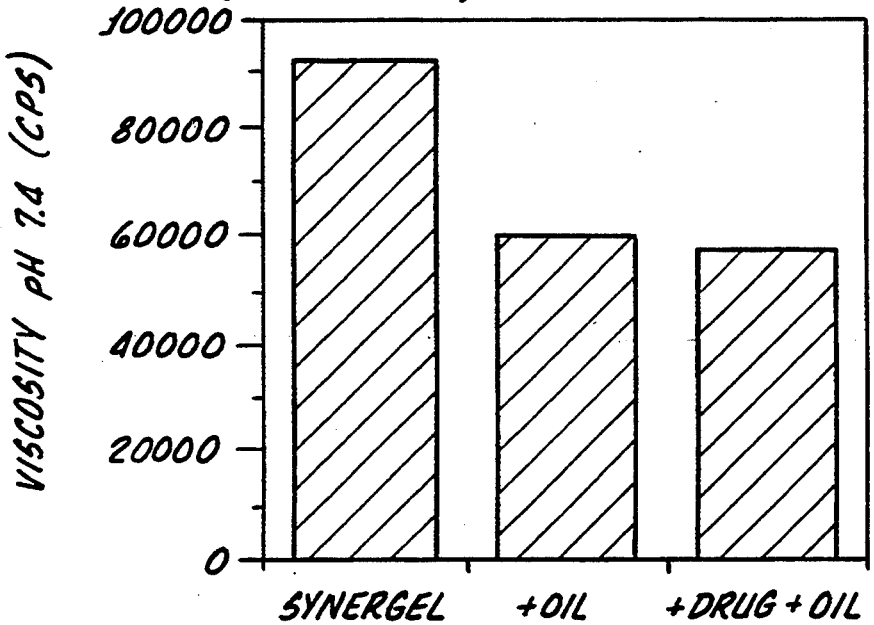
FIG. 14 is a bar graph illustrating the effect of 0.075 wt % fluorometholone on the viscosity of an emulsion of diethyl phthalate, water, Methocel and Carbopol at pH 7.4.

In order to examine the effect of fluorometholone on the viscosity of oil and water emulsions, emulsions of Methocel A4M, Carbopol 950, and diethyl phthalate were prepared and tested for viscosity at 2.66 sec$^{-1}$ at pH 4.0 and pH 7.4. Viscosities were obtained at pH 4.0 and 7.4 for the Methocel A4M, Carbopol 950 and diethyl phthalate emulsions containing 0.075% by weight flurometholone. FIG. 13 is a bar graph which illustrates the comparative viscosities of the emulsions with and without the drug at pH 4.0. FIG. 14 is a similar bar graph illustrating the comparative viscosities of the emulsions with and without the drug at pH 7.4. In the presence of the flurometholone there is a slight reduction in emulsion viscosity at pH 4, and at pH 7.4 no reduction.

Though the foregoing examples were primarily directed to ocular drug delivery vehicles, wetting agents and topical compositions, it is contemplated as being within the scope of the present invention to utilize the aqueous compositions of the present invention as drug delivery vehicles which can be administered orally or injected either subcutaneously or intramuscularly. Following injection of the free-flowing drug delivery vehicle, the aqueous compositions or emulsions will rapidly gel to form a stable drug delivery depot from which the incorporated pharmaceutical compound can diffuse.

However, it is preferred that the aqueous compositions of the present invention be utilized to deliver pharmaceutical compounds to the surface of the eye. In this manner, the pharmaceutical compounds can be retained in contact with the eye surface over an extended period of time to enhance the bioavailability of the incorporated pharmaceutical compound. Such a drug delivery method would comprise the steps of preparing the aqueous composition of the present invention containing the above described effective amount of pharmaceutical compound and introducing the composition into the lacrimal secretions of the eye. Once introduced into the cul-de-sac of the eye, the composition will rapidly gel and resist the dilution and depletion normally associated with tear turnover in the eye. The mucoadhesive gel so formed will remain in the eye for significant periods of time, slowly eroding and releasing the dissolved or emulsified pharmaceutical agent dispersed within it. This prolonged residence time leads to more effective levels of concentration of the pharmaceutical agent in the tear film and may actually result in a decrease in the overall dosage that need be administered.

Having thus described preferred exemplary embodiments of the present invention, it should be noted by those skilled in the art that the disclosures herein are exemplary only and that alternatives, adaptations and modifications may be made within the scope of the present invention. Thus, by way of example and not limitation, it is contemplated that ionic strength sensitive gelling polymers also may be utilized which thicken when exposed to changes in ionic strength. Accordingly, the present invention is not limited to the specific embodiments illustrated herein.

We claim:

1. A method for delivering a pharmaceutical compound over an extended period of time to the surface of an eye needing treatment, said method comprising the steps of:
   preparing a drop instillable aqueous and oil emulsion exhibiting the property of reversible gelation in response to substantially simultaneous variations in temperature and pH value over respective ranges between approximately 0° C. to 60° C. and pH 2.5 to pH 7.4, comprising an effective amount of a pharmaceutical compound and a stable combination of approximately 0.1% to 40% by weight of at least one thermally-sensitive gelling polymer, approximately 0.01% to 10% by weight of at least one pH-sensitive gelling polymer, and approximately 1% to 20% by weight of at least one organic oil, wherein said aqueous and oil emulsion possesses a sol-gel viscosity ranging from approximately 95 to 1,000,000 cP; and
   introducing said emulsion into the lacrimal secretions of the eye.

2. The method of claim 1 wherein said at least one thermally-sensitive gelling polymer is selected from the group consisting of alkylcellulose, hydroxyalkyl cellulose, block copolymers of polyoxyethylene and polyoxypropylene, and tetrafunctional block polymers of polyoxyethylene, polyoxypropylene, and ethylenediamine.

3. The method of claim 1 wherein said at least one thermally-sensitive gelling polymer is methylcellulose.

4. The method of claim 1 wherein said at least one pH-sensitive gelling polymer is an acidic polymer.

5. The method of claim 4 wherein said acidic polymer is a carboxyl-containing polymer.

6. The method of claim 5 wherein said carboxyl-containing polymer is a polyacrylate.

7. The method of claim 1 wherein said at least one organic oil is selected from the group consisting of mineral oils, silicone oils, fatty acid oils, triglycerides, phthalic esters, and fluorocarbon oils.

8. The method of claim 7 wherein said phthalic esters are selected from the group consisting of dimethyl phthalate, diethyl phthalate, dibutyl phthalate, and mixed di-lower alkyl phthalates.

9. The method of claim 7 wherein said fatty acid oil is peanut oil.

10. The method of claim 1 wherein said at least one thermally-sensitive gelling polymer is methylcellulose, said at least one pH-sensitive gelling polymer is a polyacrylate, and said at least one organic oil is a triglyceride of 8 to 10 carbon fatty acids.

11. The method of claim 1 wherein said emulsion comprises approximately 0.1% to 5% by weight methylcellulose, approximately 0.01% to 10% by weight polyacrylate, and approximately 5% to 15% by weight triglyceride of 8 to 10 carbon fatty acids.

12. The method of claim 1 wherein said emulsion comprises approximately 1% by weight methylcellulose, approximately 0.3% by weight polyacrylate, and approximately 10% by weight triglyceride of 8 to 10 carbon fatty acids.

13. The method of claim 1 wherein said emulsion comprises approximately 1% by weight methylcellulose, approximately 0.3% by weight polyacrylate, and approximately 10% by weight oil selected from the group consisting of peanut oil, diethyl phthalate, and dibutyl phthalate.

14. The method of claim 1 wherein said emulsion further comprises a viscosity modifying amount of a salt.

15. The method of claim 14 wherein said salt is selected from the group consisting of univalent and divalent dissociable ionic compounds.

16. The method of claim 14 wherein said salt is present in a salt-to-polymer ratio of approximately 0.001 to 0.5.

17. The method of claim 14 wherein said salt is present in a salt-to-polymer ratio of approximately 0.045 to 0.075.

18. The method of claim 1 wherein said pharmaceutical compound is oil soluble.

19. The method of claim 1 wherein said pharmaceutical compound is incorporated in a microparticulate drug delivery system.

20. The method of claim 1 wherein said pharmaceutical compound is selected from the group consisting of steroids, anti-bacterials, anti-histamines, decongestants, anti-inflammatories, miotics, anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal compounds, amoebicidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides, and lubricating agents.

21. A method for delivering a pharmaceutical compound over an extended period of time to the surface of an eye needing treatment, said method comprising the steps of:
   preparing a drop instillable aqueous and oil emulsion exhibiting the property of reversible gelation in response to substantially simultaneous variations in both temperature and pH value over respective ranges between approximately 0° C. to 60° C. and pH 2.5 to pH 7.4 comprising an effective amount of a pharmaceutical compound, approximately 0.1% to 30% by weight thermally-sensitive gelling polymer, approximately 0.01% to 10% by weight pH-sensitive gelling polymer, and approximately 1% to 20% by weight organic oil, wherein said aqueous and oil emulsion possesses a sol-gel viscosity ranging from approximately 95 cP to 1,000,000 cP; and introducing said emulsion into the lacrimal secretions of the eye.

22. The method of claim 21 wherein said temperature varies over a range between approximately 25° C. to 37° C. and said pH value varies over a range between approximately pH 4.5 to pH 7.4.

* * * * *

UNITED STATES PATENT AND TRADEMARK OFFICE
CERTIFICATE OF CORRECTION

PATENT NO. : 5,441,732
DATED : August 15, 1995
INVENTOR(S) : Hoeg et al.

It is certified that error appears in the above-indentified patent and that said Letters Patent is hereby corrected as shown below:

Column 13, line 27, delete "opol".

Column 14, line 42, delete "methylpredinisolone" and substitute therefor --methylprednisolone--.

Column 14, line 48, delete "dipivolyl" and substitute therefor --dipivalyl--.

Column 15, line 37, delete "=".

Column 20, line 25, delete "Carrimed" and substitute therefor --Carri-Med--.

Column 20, line 31, delete "solutions" and substitute therefor --solution--.

Column 20, line 37, delete "4°" and substitute therefor --4--.

Claim 1 (column 23, line 47), delete "95" and substitute therefor --95 cP--.

Signed and Sealed this

Second Day of July, 1996

Attest:

BRUCE LEHMAN

*Attesting Officer*     *Commissioner of Patents and Trademarks*